United States Patent [19]
Moriarty et al.

[11] Patent Number: 5,534,405
[45] Date of Patent: *Jul. 9, 1996

[54] ANTIBODIES, DIAGNOSTIC SYSTEMS AND METHODS FOR ASSAYING HBXAG

[75] Inventors: Ann M. Moriarty, Poway, Calif.; Hannah Alexander, Columbia, Mo.; Richard A. Lerner, La Jolla, Calif.

[73] Assignee: The Scripps Research Institute, La Jolla, Calif.

[ * ] Notice: The term of this patent shall not extend beyond the expiration date of Pat. No. 4,777,240.

[21] Appl. No.: 342,374

[22] Filed: Nov. 18, 1994

Related U.S. Application Data

[63] Continuation of Ser. No. 976,529, Nov. 16, 1992, abandoned, which is a continuation of Ser. No. 553,982, Jul. 17, 1990, Pat. No. 5,183,734, which is a division of Ser. No. 54,424, May 26, 1987, Pat. No. 4,942,125, which is a continuation-in-part of Ser. No. 648,142, Sep. 7, 1984, Pat. No. 4,777,240, which is a continuation-in-part of Ser. No. 587,570, Mar. 8, 1984, abandoned.

[51] Int. Cl.$^6$ ..................................... C12Q 1/70
[52] U.S. Cl. ..................... 435/5; 530/389.4; 436/512; 436/518; 436/820
[58] Field of Search ..................... 530/389.4; 435/5; 436/518, 820, 512

[56] References Cited

U.S. PATENT DOCUMENTS 3,791,932  2/1974  Schuurs et al. .
4,442,205  4/1984  Hamer et al. .

OTHER PUBLICATIONS

Jerne, Ann. Immunol. (Inst. Pasteur) 125 C:373 (1974).
Atassi, Immunochemistry, 12:423 (1975).
Benjamini et al., Biochemistry, vol. 8, 6:2242 (1969).
Gough, J. Mol. Biol. 165:683 (1983).
Simonsen et al., Molecular and Cellular Biology, vol. 3, 12:2250 (1983).
Pourcel, et al., Journal of Virology, vol. 42, 1:100 (1982).
Wen et al., Infect. Immun., 39 1361 (1983).
Kiyosawa et al., Hepatology, 5, 548 (1985).
Moriarty et al., Proc. Natl. Acad. Sci. USA, 78, 2606 (1981).
Tiollais et al., Nature, 317, 489 (1985).
Will et al., J. Virol., 50 335 (1984).
Elder et al., Ann Rev. Genet., 15, 295 (1981).
Moriarty et al., Antibodies to Peptides Detect New Hepatitis B Antigen: Serological Correlation with Hepatocellular Carcinoma, Science 227:429–433, 1985.
Ono, et al., Nucl. Acids Res. 11: 1747–1757 (1983).
Gerlich, et al., Cell 21: 801–809 (1980).

Primary Examiner—Mary E. Mosher
Assistant Examiner—Donna C. Wortman
Attorney, Agent, or Firm—April C. Logan

[57] ABSTRACT

Cloning and expression vectors for hepatitis B HBxAg, cell cultures containing those vectors, polypeptides related to HBxAg, and diagnostic systems and methods for assaying for the presence of HBxAg and anti-HBxAg antibodies in a body sample are disclosed.

16 Claims, 9 Drawing Sheets

Restriction Map of SV40 DNA

Restriction Map of pBR322 DNA

FIG. 6

HBV-X gene (154 a.a.)

Met–Ala–Ala–Arg–Leu–Cys–Cys–Gln–Leu–Asp–Pro–Ala–Arg–Asp–Val–Leu–Cys–Leu–Arg–Pro

↓SVHBV.3 start

Val–Gly–Ala–Glu–Ser–Cys–Gly–Ser–Pro–Phe–Ser–Gly–Ser–Leu–Gly–Thr–Leu–Ser–Ser–Pro

Ser–Pro–Ser–Ala–Val–Pro–Thr–Asp–His–Gly–Ala–His–Leu–Ser–Leu–Arg–Gly–Leu–Pro–Val

Cys–Ala–Phe–Ser–Ser–Ala–Gly–Pro–Cys–Ala–Leu–Arg–Phe–Thr–Ser–Ala–Arg–Arg–Met–Glu

Thr–Thr–Val–Asn–Ala–His–Gln–Ile–Leu–Pro–Lys–Val–Leu–His–Lys–Arg–Thr–Leu–Gly–Leu

Ser–Ala–Met–Ser–Thr–Thr–Asp–Leu–Glu–Ala–Tyr–Phe–Lys–Asp–Cys–Leu–Phe–Lys–Asp–Trp peptide 99

Glu–Glu–Leu–Gly–Glu–Glu–Ile–Arg–Leu–Lys–Val–Phe–Val–Leu–Gly–Gly–Cys–Arg–His–Lys peptide 100

Leu–Val–Cys–Ala–Pro–Ala–Pro–Cys–Asn–Phe–Phe–Thr–Ser–Ala peptide 142

ANTIBODIES, DIAGNOSTIC SYSTEMS AND METHODS FOR ASSAYING HBXAG

This invention was made with government support from the National Institutes of Health. The government may have certain rights in the invention.

CROSS-REFERENCE TO RELATED APPLICATIONS

This is a continuation of application Ser. No. 07/976,529 filed on Nov. 16, 1992, (abandoned), which is a continuation of application Ser. No. 07/553,982 filed on July 17, 1990, (now U.S. Pat. No. 5,183,734), which is a divisional of application Ser. No. 07/054,424 filed on May 26, 1987 (now U.S. Pat. No. 4,942,125), which is a continuation-in-part of application Ser. No. 06/648,142 filed on Sep. 7, 1984 (now U.S. Pat. No. 4,777,240), which is a continuation-in-part of application Ser. No. 06/587,570 filed on Mar. 8, 1984 (abandoned), the disclosures of which are herein incorporated by reference.

DESCRIPTION

TECHNICAL FIELD

The present invention relates to recombinant DNA technology, expression vectors, and polypeptide expression markers, and more specifically to the cloning of the gene for hepatitis B HBxAg, an expression vector containing HBxAg as well as assay systems and methods for determining the presence of HBxAg and anti-HBxAg in body samples.

BACKGROUND ART

A. Cloning and Vectors

The introduction of exogenous DNA into eucaryotic cells has become one of the most powerful tools of the molecular biologist. This process requires efficient delivery of the DNA into the nucleus of the recipient cell and subsequent identification of cells that are expressing the foreign DNA.

Engineered vectors such as plasmids or bacteriophages (phages) or other DNA sequence that is able to replicate in a host cell can be used to construct cells that act as factories to produce large amounts of specific viral proteins. Recombinant plasmids will be used herein as exemplary vectors, also called cloning vehicles. See U.S. Pat. No. 4,338,397, incorporated herein by reference.

Plasmids are extrachromosomal genetic elements found in a variety of bacterial species. They are typically double-stranded, closed, circular DNA molecules. The most widely used plasmid is pBR322, a vector whose nucleotide sequence and endonuclease cleavage sites are well known.

Nucleic acid production using plasmid or phage vectors has become very straightforward. The plasmid or phage DNA is cleaved with a restriction endonuclease and joined in vitro to a foreign DNA of choice. The resulting recombinant plasmid or phage is then introduced into a cell such as E. coli, and the cell so produced is induced to produce many copies of the engineered vector. Once a sufficient quantity of DNA is produced by the cloning vector, the produced foreign DNA is excised and placed into a second vector to produce or transcribe the protein or polypeptide encoded by the foreign gene.

Depending on the DNA (intact gene, cDNA, or bacterial gene), it may be necessary to provide eucaryotic transcription and translation signals to direct expression in recipient cells. These signals may be provided by combining the foreign DNA in vitro with an expression vector.

Expression vectors contain sequences of DNA that are required for the transcription of cloned genes and the translation of their messenger RNA's (mRNA's) into proteins. Typically, such required sequences or control elements are: (1) a promoter that signals the starting point for transcription; (2) a terminator that signals the ending point of transcription; (3) an operator that regulates the promotor; (4) a ribosome binding site for the initial binding of the cells' protein synthesis machinery; and (5) start and stop codons that signal the beginning and ending of protein synthesis.

To be useful, an expression vector should possess several additional properties. It should be relatively small and contain a strong promoter. The expression vector should carry one or more selectable markers to allow identification of transformants. It should also contain a recognition site for one or more restriction enzymes in regions of the vector that are not essential for expression.

The construction of expression vectors is, therefore, a complicated and somewhat unpredictable venture. The only true test of the effectiveness of an expression vector is to measure the frequency with which the synthesis of the appropriate mRNA is initiated. However, quantitation of mRNA is tedious, and it is often difficult to obtain accurate measurements. Other more practicable means have, therefore, been developed to detect transformation.

One such means has been to monitor synthesis of foreign proteins in transformed cells with enzymatic assays. Several marker genes have been developed for indicating that transformation has occurred.

Another means used to monitor transformation involves the use of immunological reagents. If the level of expressed protein is sufficiently high, then cytoplasmic or surface immunofluorescence with an antibody conjugated to a fluorescent dye such as fluorescein or rhodamine may be used to detect vector-specific protein expression products.

More commonly, transformed cells are cultured in the presence of radioactivity after immunoprecipitation. This approach has used *Staphylococcus aureus* (*S. aureus*) protein A selection of immune complexes (Kessler, (1975), *J. Immunol.*, 115: 1617–1624) and the Western blotting procedure (Renart et al., (1979), *Proc. Natl. Acad. Sci. USA*, 76: 3116–3120) to detect transformation-specific markers.

Analysis of gene expression using Simian Virus 40 (SV40) vectors is by far the most explored eucaryotic transformation technique at the biological and immunochemical levels. Genetic and biochemical information relating to the organization of the SV40 genome has been established or confirmed by the nucleotide sequence of the viral genome. Review by Tooze (1980), *Molecular Biology of Tumor Viruses,* 2nd ed., Part 2, Cold Spring Harbor Laboratory, Cold Spring Harbor, N.Y. The design of different SV40 vector molecules has relied on the accurate mapping of genetic signals and the use of restriction endonucleases for the isolation of defined fragments from the SV40 genome.

SV40 was developed initially as a eucaryotic-transducing vector using a lytic system. Mulligan et al., (1929), *Nature* (London), 277: 108–114. Subsequently, transforming (nonlytic) vectors were constructed with isolated segments of the SV40 genome. Review by Elder et al., (1981), *Annu. Rev. Genet.*, 15: 295–340.

Hamer et al. were the first to suggest that SV40 might be used to clone genes for which no probe was available. They suggested double-stranded cDNA copies from a heterogeneous mRNA population could be "shotgunned" into an SV40 vector, and virus carrying the desired sequence could be identified by using a radioactive or fluorescent antibody.

Hamer et al. first reported the construction of an SV40 recombinant expression vector containing an expression marker in 1979. Hamer et al., (1979), *Cell*, 17: 725–735. Their SV40 vector contained the viral DNA sequences from the Bam HI endonuclease restriction site at 0.14 map units clockwise to the HaeII restriction site at 0.82 map units. In addition to the entire early gene A and the origin of viral DNA replication, the vector contained the viral promoter, leader, intervening sequence, 5' portion of the body and 3' terminal sequences for the viral late 19S mRNA. It did not contain 1660 base pair (bp) of late region sequences encoding the viral protein UPI, 2 and 3. Priers et al., (1978), *Nature*, 273: 113–120 and Reddy et al., (1978), *Science*, 200: 494–502.

Rabbit beta-globin gene coding sequences were ligated into the above vector as an expression marker. To determine whether rabbit beta-globin was being synthesized in monkey cells infected with their recombinant vector, Hamer et al., supra, used a radioimmunoassay capable of detecting as little as 1.0 nanogram of globin.

Although Hamer et al. were able to demonstrate positive evidence of beta-globin expression, they expressed several reservations as to the utility of the SV40/beta-globin recombinant system. First, since globin is only sparingly soluble, significant losses may have been sustained during the preparation of samples for measurement. Thus, the determination of the amount of globin in the infected cells may be in error by as much as 10-fold. Second, the assay cannot distinguish between authentic globin and other immunologically-related products, such as read-through protein or polypeptide fragments.

A factor that Hamer et al. did not address is the high degree of homology between all eucaryotic globins. This homology makes it difficult to distinguish vector-induced globin expression from globin endogenous to the host cell system.

B. Hepatitis B Virus Peptides and Anti-Polypeptide Antibodies

The hepatitis viruses are markedly different agents. They are grouped together strictly by virtue of the "target" organ the affect, the liver. Although a number of viruses affect the liver as part of systemic infections, the term "hepatitis viruses" is usually taken to mean Type A (HAV), Type B (HBV), and the non-A, non-B agents. Of the three types of viruses, HBV is by far the most explored at the biological, immunochemical, and clinical levels.

HBV is classified as a DNA virus and differs in many respects from all other families of DNA viruses. HBV is composed of an outer coat (more substantial than a membrane or envelope) consisting of protein, lipid, and carbohydrate, and bearing a unique antigen complex; i.e., the hepatitis B surface antigen (HBsAg). It also contains an inner-nucleocapsid with an antigenic specificity distinct from that of the surface antigen; i.e., the hepatitis B core antigen (HBcAg).

A soluble antigen, HBeAg, is also recognized in the art. This antigen is thought to consist of HBcAg polypeptides that are not assembled into HBV cores, and consequently have a unique antigenic specificity in the unassembled state.

In typical self-limiting acute HBV infections, the following serological markers appear sequentially in serum of an infected host: HBsAg, HBeAg, anti-HBC, anti-HBE, and anti-HBS. The appearance of anti-HBE signals the eventual loss of detectable HBsAg. This is true in all cases of self-limited acute HBV infection. Following the disappearance of HBS, there is a delay of from a few weeks to several months before the appearance of anti-HBS.

During chronic HBV infection, HBsAg and anti-HBC are present. The host's serum can show either the HBeAg or anti-HBE serological markers; i.e. the patient can either be HBeAg or anti-HBE positive.

Sensitive and specific radioimmunoassays and enzyme immune assays for several of the HBV markers are in wide use. These highly sensitive serologic tests have provided a basis for monitoring the appearance of virus and immune response markers during the course of HBV infection.

In the past few years, many studies have indicated that each serologic marker signifies specific viral events for host responses during HBV replication. The profile of serologic markers at various stages during the clinical course of disease can thus offer useful diagnostic and prognostic information.

The association between hepatitis B virus and human hepatocellular carcinoma (HCC), liver cancer, has been extensively studied, and seroepidemiological as well as histopathological findings strongly suggest that HBV is directly or indirectly involved in the etiology of liver cancer. A number of hepatoma cell lines have been derived from human HCC, and detection of HBV-specific DNA integrated into the genome of two such cell lines, PLC/PRF/5 and EPH3B, have been reported. However, in these cell lines, only the hepatitis B surface antigen has been expressed in tissue culture as a virus-specific gene product. Other markers of HBV such as hepatitis B core antigen, hepatitis BE antigen, and a DNA polymerase have not been detected.

Some DNA tumor viruses of animals can produce transformation through the action of viral genes that regulate the replication and integration of the viral genome, and transformed cells by such viruses can bear a T (tumor) or neo(new) antigen expressed by the transforming genes. Recent evidence for an antigen analogous to T antigen has been obtained in human hepatoma cells containing integrated HBV genes using the anti-complement immunofluorescent staining technique. This antigen has been designated HBV-associated nuclear antigen (HBNA). Wen et al., (1983) *Infect. Immun.*, 39: 1361–1367.

HBNA was detected in sera from several HBsAg-positive HCC patients, and expression of the antigen was demonstrated in both cell culture and tumor tissue. In addition, anti-HBNA antibodies were found in the sera of some HBsAg-positive patients with HCC. HBNA may represent the previously unrecognized expression of an HBV gene.

In 1979 Galibert et al., *Nature*, 281: 646–650, reported the nucleotide sequence of the HBV genome, a circular DNA of about 3200 bases that is part double- and part single-stranded, a feature unique among viruses. The long or L strand (completely circular) of the genome was found to contain four reading frames large enough to account for viral proteins. These regions were termed S, C, P and X, and are shown schematically in FIG. 1. Regions S and C have been found to contain the genes for HBsAg and HBcAg respectively. Region P is thought to code for a protein similar in size and amino acid residue content to a DNA polymerase.

Region X was postulated by Wen et al., supra, to be one of the probable sources of the gene coding for HBNA.

The mere tentative assignment of functions for the genes in regions P and X demonstrates the gap that still exists in understanding the genetic organization and molecular biology of HBV. A reason for this gap has been the absence of an in vitro system for propagation of the virus.

Until recently, the only source of HBV was the serum of human patients. The failure of attempts to grow the virus in cell culture is the result of its very narrow host cell range.

One approach to the problem of producing HBV DNA and its gene products has been to use recombinant DNA technology. This technology enables the large scale production of the nucleic acid sequences that code for a particular viral protein.

Tiollais et al. (1981), *Science*, 213:406–411 reported transformation of *E. coli* with pBR322 containing the gene coding for HBsAg, and reported production of significant quantities of that isolated gene. Those workers also wanted to study the HBsAg gene's location within the HBV genome, and the factors that affected its expression into protein. To do this they constructed expression vectors containing the HBsAg gene for use in both bacterial and mammalian cells.

One of the expression vectors constructed by Tiollais et al., supra, achieved bio-synthesis of a protein in *E. coli* that contained HBsAg antigenic determinants. It was built by inserting a portion of the gene coding for HBsAg into the bacteriophage plac5-1UV5 so as to conserve the reading frame of natural HBV. In order to study HBV gene expression in mammalian cells Tiollais et al., supra, constructed a series of HBsAg-expression plasmids by inserting transfection elements at various locations within the whole HBV genome. The transfection elements allowed the entire HBV genome to be integrated in several different orientations into the genome of mouse cells transformed with the vector. In creating the vectors in this way those workers attempted to use HBV's naturally occurring genetic control elements.

Only three of the six expression vectors reported by Tiollais et al., supra, produced expression of the desired HBsAg protein. Its production was detected by testing for its presence in tissue culture fluids using sheep anti-HBsAG antiserum. The other viral markers known at the time of the study (i.e., HBcAg, HBeAg and DNA polymerase) were not detected in the transformed cells.

At the time of the above Tiollais et al. study, the possible existence of Region X was known as was the possibility that it may code for a HBV protein. That is, it was known that the HBV genome contained a capacity to code for more proteins than had been previously associated with the virus.

This problem has been called genotype in search of phenotype. It is this problem, inter alia, that Wen et al., supra, were addressing when they postulated Region X as containing the gene coding for HBNA.

Prior to the above Tiollais et al. and Wen et al. studies, Sutcliffe et al., (1980) *Nature*, 287: 801–805, demonstrated, inter alia, a general technique for solving this problem. They chemically synthesized a polypeptide from within the protein predicted by the nucleotide sequence of a viral gene whose protein product was unknown. Antibodies were raised to the polypeptide and were reacted against all the proteins made by cells infected with the virus. Using antibodies to portions of a predicted protein, Sutcliffe et al. detected a previously unknown and unrecognized viral protein product.

To date, the use of this or any other technique to unequivocally identify the protein product of HBV genome Region X has not been reported. This may be because while the general concept of preparing synthetic antigens and using them to induce antibodies of predetermined specificity has been described, there remains a large area of this technology that continues to defy predictability.

The reasons for this are several. First, protein amino acid residue sequences deduced from a genetic sequence are of a hypothetical nature unless the nucleotide sequence reading frame is firmly established because of the redundancy of the genetic code.

Second, a synthetic antigen does not necessarily induce antibodies that immunoreact with the intact protein in its native environment. Third, a host's natural antibodies to an immunogen rarely immunoreact with a polypeptide that corresponds to a short linear portion of the immunogen's amino acid sequence.

BRIEF SUMMARY OF THE INVENTION

The present invention contemplates several aspects. One aspect is a recombinant DNA comprising an expression vector linked to the gene coding for HBxAg. In a particularly preferred recombinant DNA, the DNA expression vector comprises a first DNA sequence comprising the Simian Virus 40 viral DNA sequence from the Bam HI endonuclease restriction site at base position 2468 clockwise to the Hae II endonuclease restriction site at base position 767 according to FIG. 2, and the gene coding for HBxAg is provided by a second gene DNA sequence comprising the hepatitis B virus DNA sequence from the Hae II endonuclease restriction site at base position 1437 clockwise to the Bam HI endonuclease restriction site at base position 28 according to FIG. 1. The first and second DNA sequences are operatively linked to promote expression of HBxAg.

Another aspect of this invention is constituted by a recombinant DNA that comprises a gene coding for HBxAg or for a polypeptide constituting a substantial portion of HBxAg. A particularly preferred recombinant DNA contains the gene coding for HBxAg and has the base sequence shown in FIG. 1 as covering base positions 1437 clockwise to 28, or a substantial portion thereof.

A plasmid coding for at least one recombinant DNA that comprises a gene coding for HBxAg or for a polypeptide constituting a substantial portion thereof constitutes another aspect of this invention. That plasmid may include the base sequence shown in FIG. 1 as covering base positions 1437 clockwise to 28, or a substantial portion thereof. In particularly preferred practice, the plasmid comprises a first DNA sequence comprising the Simian Virus 40 (SV40) viral DNA sequence from the Bam HI endonuclease restriction site at base position 2468 clockwise to the Eco RI endonuclease restriction site at base position 1717 according to FIG. 2; a second DNA sequence comprising the plasmid pBR322 DNA sequence from the Bam HI endonuclease position at base position 375 clockwise to the Eco RI endonuclease restriction site at base position zero according to FIG. 3; and a third DNA sequence comprising the hepatitis B virus DNA sequence from the Bam HI endonuclease restriction site at base position 1400 clockwise to the Bam HI endonuclease restriction site at base position 28 according to FIG. 1. In that plasmid, the first and second DNA sequences are operatively ligated at their respective Eco RI endonuclease restriction sites; the second and third DNA sequences are operatively ligated at their respective Bam HI endonuclease restriction sites; and the first and third DNA sequences are operatively ligated at their respective Bam HI endonuclease restriction sites according to FIG. 4.

A method of producing HBxAg or a substantial polypeptide portion of HBxAg constitutes another aspect of this invention. According to this aspect, a host containing an expression system of this invention is grown in a culture broth medium until HBxAg or a substantial polypeptide portion thereof is produced and accumulated in the host or culture broth. The accumulated HBxAg or the substantial polypeptide portion thereof is thereafter recovered.

Yet another aspect of this invention contemplates an antigenic synthetic polypeptide. That synthetic polypeptide contains about 6 to about 40 amino acid residues and corresponds in sequence to the sequence of an antigenic determinant of HBxAg. A particularly preferred polypeptide includes an amino acid residue sequence selected from the group of polypeptide sequences represented by the formulae written from left to right and in the direction of amino-terminus to carboxy-terminus:

(i) Leu-Ser-Ala-Met-Ser-Thr-Thr-Asp-Leu-Glu-Ala-Tyr-Phe-Lys-Asp;

(ii) Leu-Phe-Lys-Asp-Trp-Glu-Glu-Leu-Gly-Glu-Glu-Ile-Arg-Leu-Lys-Val;

(iii) Ala-Pro-Ala-Pro-Cys-Asn-Phe-Phe-Thr-Ser-Ala;

(iv) Gln-Leu-Asp-Pro-Ala-Arg-Asp-Val-Leu-Cys-Leu-Arg-Pro-Val-Gly;

(v) Ser-Ala-Val-Pro-Thr-Asp-His-Gly-Ala-His-Leu-Ser-Leu-Arg-Gly-Leu-Pro-Val-Cys; and (vi) Met-Glu-Thr-Thr-Val-Asn-Ala-His-Gln-Ile-Leu-Pro-Lys-Val-Leu-His-Lys-Arg-Thr-Leu-Gly.

A water-soluble or water-dispersible antigenic polymer containing a plurality of joined synthetic polypeptide repeating units bonded together by oxidized cysteine residues is also contemplated herein. The repeating units are comprised of the polypeptides discussed hereinabove that contain cysteine residues at both the amino- and carboxy-termini, or contain one cysteine residue at one terminus and one cysteine residue within the polypeptide chain. Particularly preferred polypeptide repeating units, including the amino- and carboxy-terminal cysteine residues, are represented by a formula, written from left to right and in the direction from amino-terminus to carboxy-terminus, selected from the group consisting of Cys-Leu-Ser-Ala-Met-Ser-Thr-Thr-Asp-Leu-Glu-Ala-Tyr-Phe-Lys-Asp-Cys;

Cys-Leu-Phe-Lys-Asp-Trp-Glu-Glu-Leu-Gly-Glu-Glu-Ile-Arg-Leu-Lys-Val-Cys;

$R^1$-Ala-Pro-Ala-Pro-Cys-Asn-Phe-Phe-Thr-Ser-Ala-$R^2$;

$R^1$-Gln-Leu-Asp-Pro-Ala-Arg-Asp-Val-Leu-Cys-Leu-Arg-Pro-Val-Gly-$R^2$;

Cys-Ser-Ala-Val-Pro-Thr-Asp-His-Gly-Ala-His-Leu-Ser-Leu-Arg-Gly-Leu-Pro-Val-Cys; and Cys-Met-Glu-Thr-Thr-Val-Asn-Ala-His-Gln-Ile-Leu-Pro-Lys-Val-Leu-His-Lys-Arg-Thr-Leu-Gly-Cys, wherein each of $R^1$ and $R^2$ is a cysteine residue, with the proviso that only one of $R^1$ and $R^2$ is present.

Receptor molecules that include an antibody combining site such as antibodies capable of immunoreacting with one of the before-mentioned antigenic polypeptides are also contemplated herein. The particularly preferred polypeptides with which these receptor molecules immunoreact are illustrated by the polypeptides described hereinbefore. These receptor molecules also immunoreact with HBxAg or with a substantial polypeptide portion thereof.

A diagnostic assay system for determining the presence of a detectable amount of HBxAg in a body sample to be assayed is also contemplated. This system comprises at least one container that contains a reagent that includes the above-described receptor molecules. This system may further include a second reagent in a second container, which second reagent is the antigenic synthetic polypeptide with which the receptor molecules immunoreact. A means for signalling the immunoreaction between the receptor molecules and HBxAg may constitute a further part of the diagnostic assay system.

A method for assaying for the presence of a detectable amount of HBxAg in a body sample constitutes a further aspect of this invention. Here, proteins from a body sample to be assayed for the presence of a detectable amount of HBxAg are admixed with the above receptor molecules in the presence of an indicating means for signalling an immunoreaction between the receptors and HBxAg. The admixture is maintained for a time period sufficient for the indicating means to signal that an immunoreaction has occurred. The presence of that signal is then ascertained.

BRIEF DESCRIPTION OF THE DRAWINGS

In the Figures forming a portion of the disclosure of this invention:

FIG. 6 illustrates the translated amino acid residue sequence shown from left to right and in the direction from amino-terminus to carboxy-terminus of the gene coding for HBxAg. The substantial portion of HBxAg expressed by SVBHV-3 is illustrated by the arrow at amino acid residue position 23 (Ala), which is the amino-terminal residue of the expressed HBxAg polypeptide. The relative positions of synthetic polypeptides designated 8, 42, 79, 99, 100 and 142 of this invention in the HBxAg sequence are illustrated by the three labeled, underlined amino acid residue sequences. The amino acid residue sequence of synthetic polypeptide 99 therefore corresponds to positions 100 through 115 from the amino-terminal Met residue shown in the Figure, the sequence of synthetic polypeptide 100 corresponds to positions 115 through 131 from the amino-terminal Met residue of the Figure, and the sequence of synthetic polypeptide 142 corresponds in sequence to positions 144 through 154 from the amino-terminal Met residue of the Figure; i.e., the eleven carboxy-terminal residues.

Figure 1:
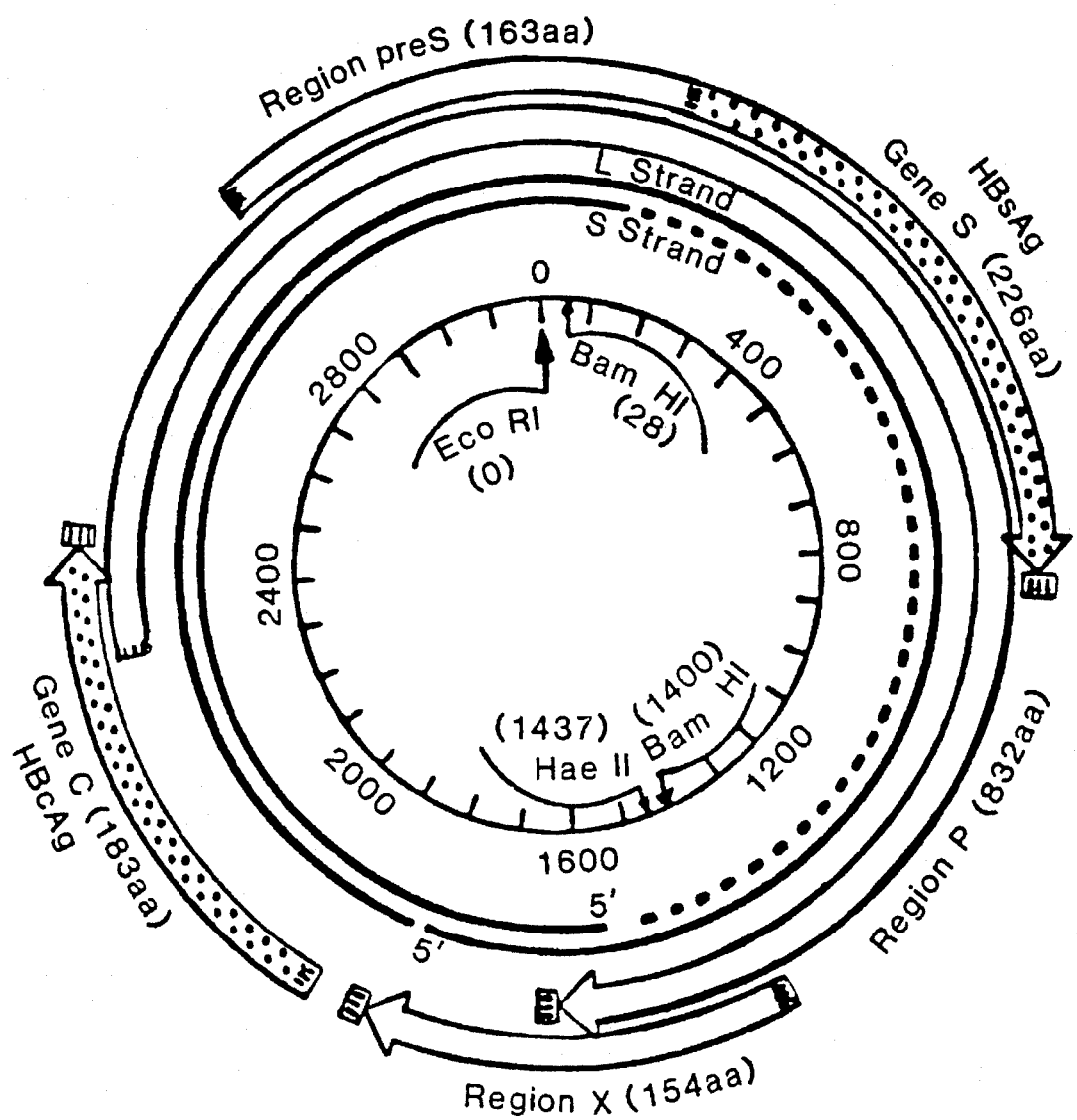
FIG. 1 is a schematic diagram showing the physical structure and genetic organization of the HBV/adw genome from Tiollais et al. (1981), *Science*, 213:406–411 as modified by Ono et al. (1983), *N.A.R.*, 11: 1747–1757. The 5'-end of the long (L) strand is reported to be base paired with the 5'-end of the short (S) strand. Certain restriction sites indicated by arrows linked to arcs and the abbreviation for the restriction endonuclease correspond to the physical map of the HBV/adw genome analyzed by Ono et al., supra. The broad arrows surrounding the genome correspond to the four large, open regions of the L strand. These four potential coding regions are designated S, P, X and C. The number of amino acid residues in parentheses (aa) following each of the four designated regions corresponds to the length of the hypothetical polypeptide encoded by each region. The two regions corresponding to the defined genes S and C are indicated by dotted areas within the broad arrows. The single Eco RI endonuclease cleavage site is used as the point of origin of the map.
Figure 2:
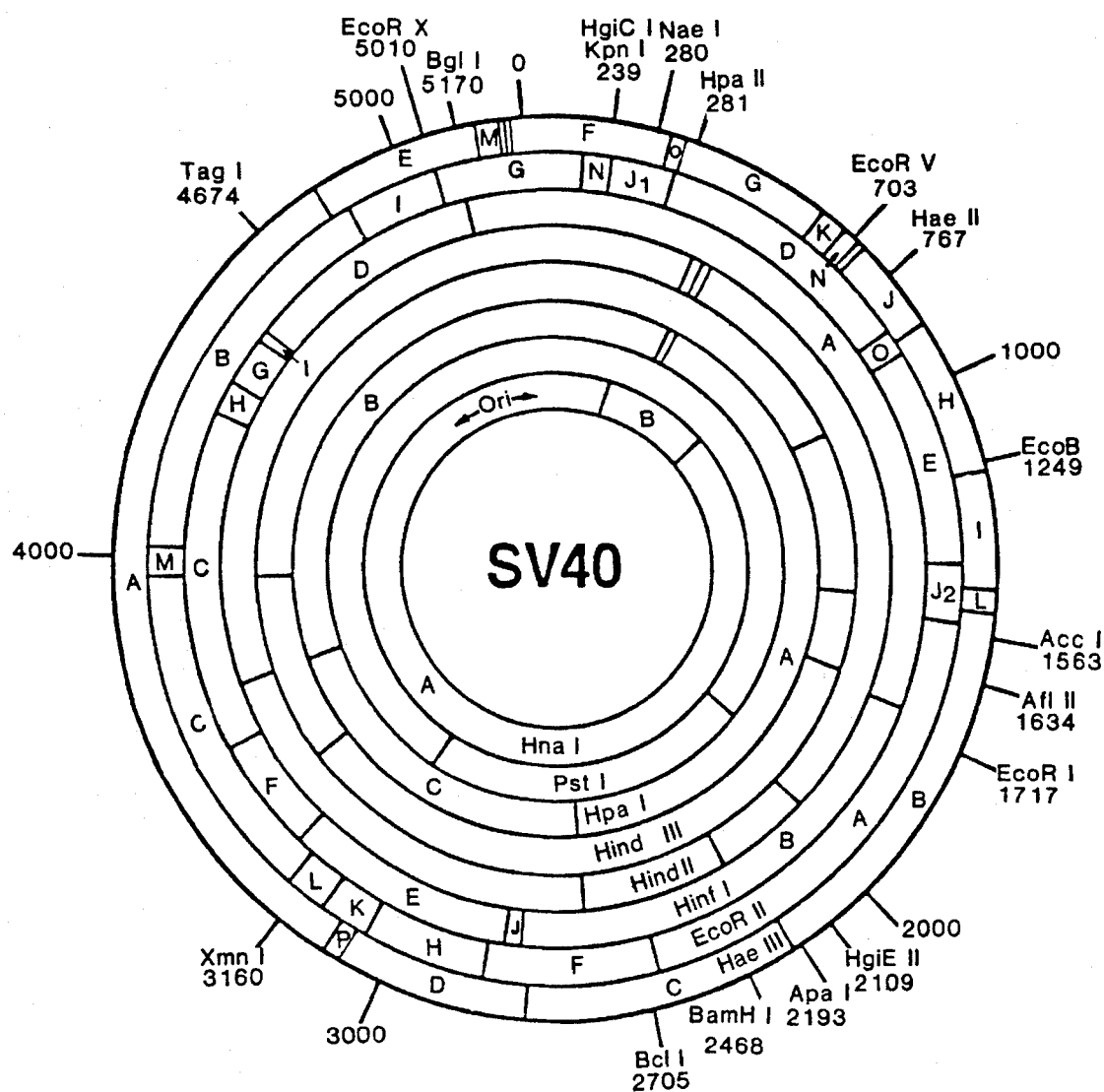
FIG. 2 schematically illustrates an SV40 DNA restriction map prepared from the primary sequence published by Reddy et al. (1978), *Science*, 200: 494–501, as modified by Van Heuverswyn and Fiers (1979), *Eur. J. Biochem.*, 100: 51–60.

The radiolabeled cell lysates were loaded onto denaturing sodium dodecyl sulfate-polyacrylamide gels (12.5%) (SDS-PAGE), and subjected to electrophoresis following the procedures of Laemmli, (1970), *Nature*, 297: 680: 685. The proteins were electrophoretically transferred to nitrocellulose sheets as described by Towbin et al. (1979), *Proc. Natl. Acad. Sci. USA* 76: 4350–4354. The nitrocellulose blots were stained in amido black prior to incubation at 4° C. overnight in BLOTTO (Johnson et al. (1983), *J. Exp. Med.* 159: 1751–1756) for reduction of non-specific binding. Nitrocellulose strips were incubated for 3 hours at room temperature with a 1:350 dilution of anti-polypeptide antibodies in a final volume of 10 ml BLOTTO. The strips were washed in BLOTTO prior to a 1 hour incubation with $^{125}$I-labeled *S. aureus* protein A (10$^6$ cpm per 10 ml). Where competition by a polypeptide is indicated below, the anti-polypeptide antisera were incubated with 100 micrograms polypeptide for 60 minutes prior to the addition of the radiolabeled antigen. The strips were washed as above, rinsed with water, dried and autoradiographed. Lanes 1 and 5 were reacted with anti-polypeptide 99 antibodies (anti-99); lane 2 was reacted with anti-99 preincubated with polypeptide 99; lane 3 was reacted with anti-99 preincubated with a non-related polypeptide; and lane 4 was reacted with a preimmune serum control. Lysates from HepG2 cells lanes 1–4) did not react with anti-polypeptide 99. The numerals on the left-hand margin indicate relative protein migration positions. Arrows at the right-hand margin indicate the migration positions of proteins having molecular weights of 28,000 and 45,000 daltons.

Figure 7:
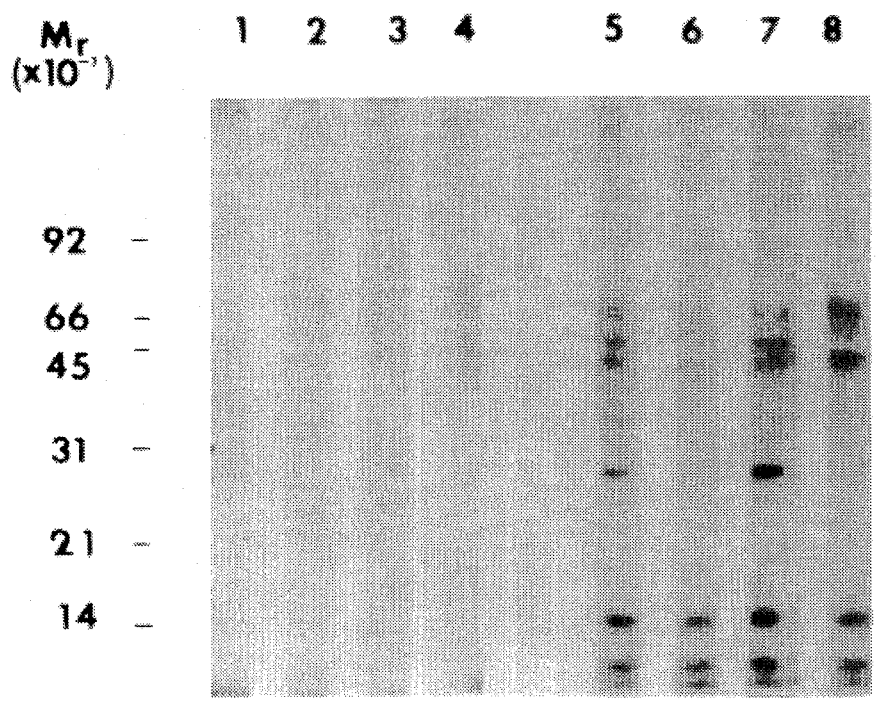
FIG. 7 is a photograph of an autoradiogram showing the reactivity of anti-X antisera with two human hepatoma cell lysates. Two human hepatoma cell lines, PLC/PRF/5 and HepG2 were grown in Dulbecco's Modification of Eagle's Medium (DMEM) with 10% fetal calf serum to subconfluency (day 6 of a 1:5 split from a confluent culture). Supernatants were removed, the flasks containing the monolayers were placed on ice for 5 minutes before the cells were collected by scraping, and the collected cells were pelleted by centrifugation. Cell pellets were washed with phosphate buffered saline (PBS), quick frozen at −70° C. and lyophilized overnight. The resultant cell powders were dissolved in PBS and brought to a final concentration of 2 milligrams per milliliter (mg/ml) in sample buffer. The samples were boiled for 5 minutes, and cell debris was removed by centrifugation in a Beckman microfuge for 30 minutes. Fifty micrograms of cell lysate were incubated for 15 minutes in RIPA buffer (PBS, containing 1% Nonidet P-40 (polyoxyethylene (9) octyl phenyl ether), 0.05% sodium deoxycholate and 0.1% SDS) and radiolabeled with 3 micro-Curies of $^{125}$I by the chloramine T reaction McConahey et al. (1966), *Int. Arch. Allergy* 29: 185–189. 1.5×10$^6$ counts per minute (cpm) of each of the radiolabeled hepatoma lysates were reacted with 10 microliters of anti-X polypeptide for 60 minutes in RIPA. The antigen-antibody complexes (immunoreaction-products) were precipitated with formalin-fixed *Staphylococcus aureus*. The pellets were washed once with RIPA and twice with 500 millimolar (mM) LiCl, 100 mM Tris (pH=8.5), and were analyzed for radioactivity. All pellets were dissolved in 40 microliters sample buffer (0.0625M Tris-HCl (pH 6.8), 2% SDS, 10% glycerol, 5% 2-mercaptoethanol and 0.001% bromophenol blue), boiled for 3 minutes, centrifuged to remove cell debris and subjected to SDS-PAGE as follows.
Figure 8:
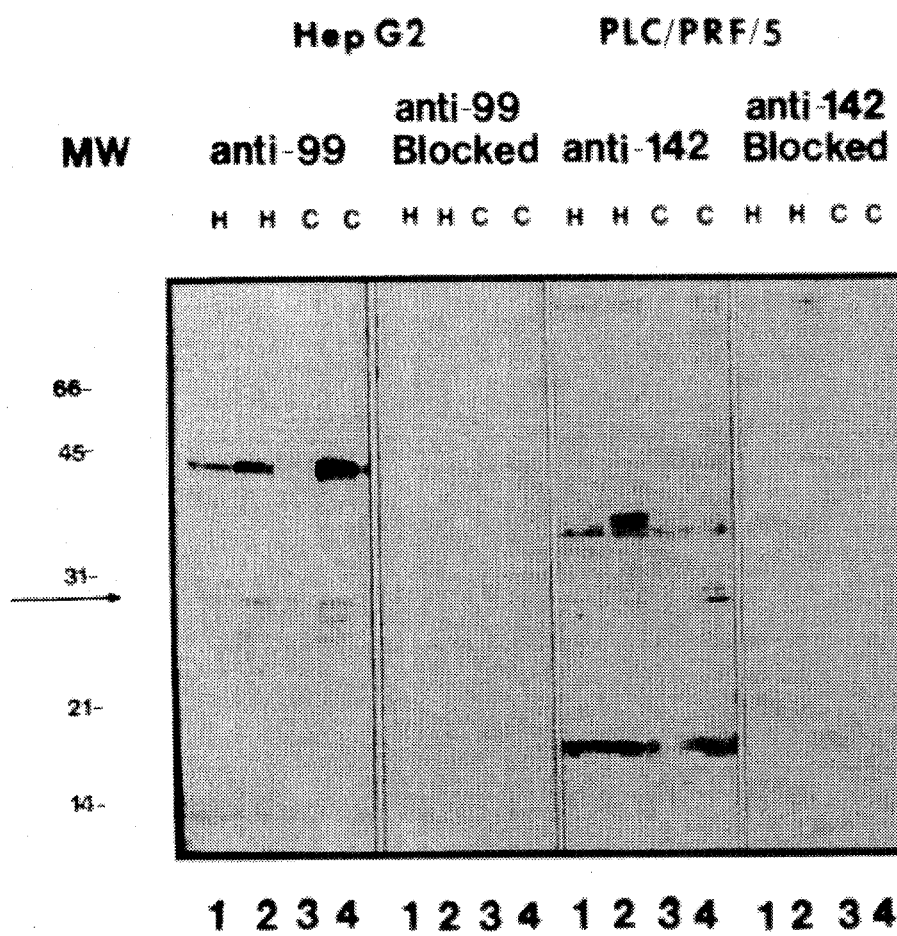

FIG. 8 is a photograph showing the reactivity of anti-X antiserum with chimpanzee (C; lanes 3 and 4) and human (H; lanes 1 and 2) liver tissues. Liver sections from chimpanzees and humans were snap frozen in liquid nitrogen and were ground into a fine powder with a mortar and pestle. Cell powders were solubilized in sample buffer, and were subjected to gel electrophoresis and blotted as described for FIG. 7. Nitrocellulose strips were developed with a 1:50 dilution of antiserum as described in FIG. 7, with two exceptions: 1) 1% bovine serum albumin (BSA) solution was used in place of BLOTTO in all incubations and washes, and 2) the antigen-bound antibodies were detected with horseradish peroxidase conjugated goat anti-rabbit IgG. The antigen-antibody immunoreaction products were visualized by dipping the strips into the following developing solution. The developing solution was prepared from 50 ml of TBS buffer at 37° C. to which were added 250 microliters of absolute ethanol containing 8 mg of 4-chloro-1-naphthol and 330 microliters of 30 percent hydrogen peroxide. Antiserum to polypeptide 99 (anti-99) was used in the two left-hand panels, blocked and not blocked, while antiserum to polypeptide 142 (anti-142) was used in two right-hand panels, blocked and not blocked. Numerals on the left-hand side of the Figure illustrate gel migration positions for proteins having molecular weights of 66, 45, 31, 21 and 14 kilodaltons, respectively.

Figure 9:
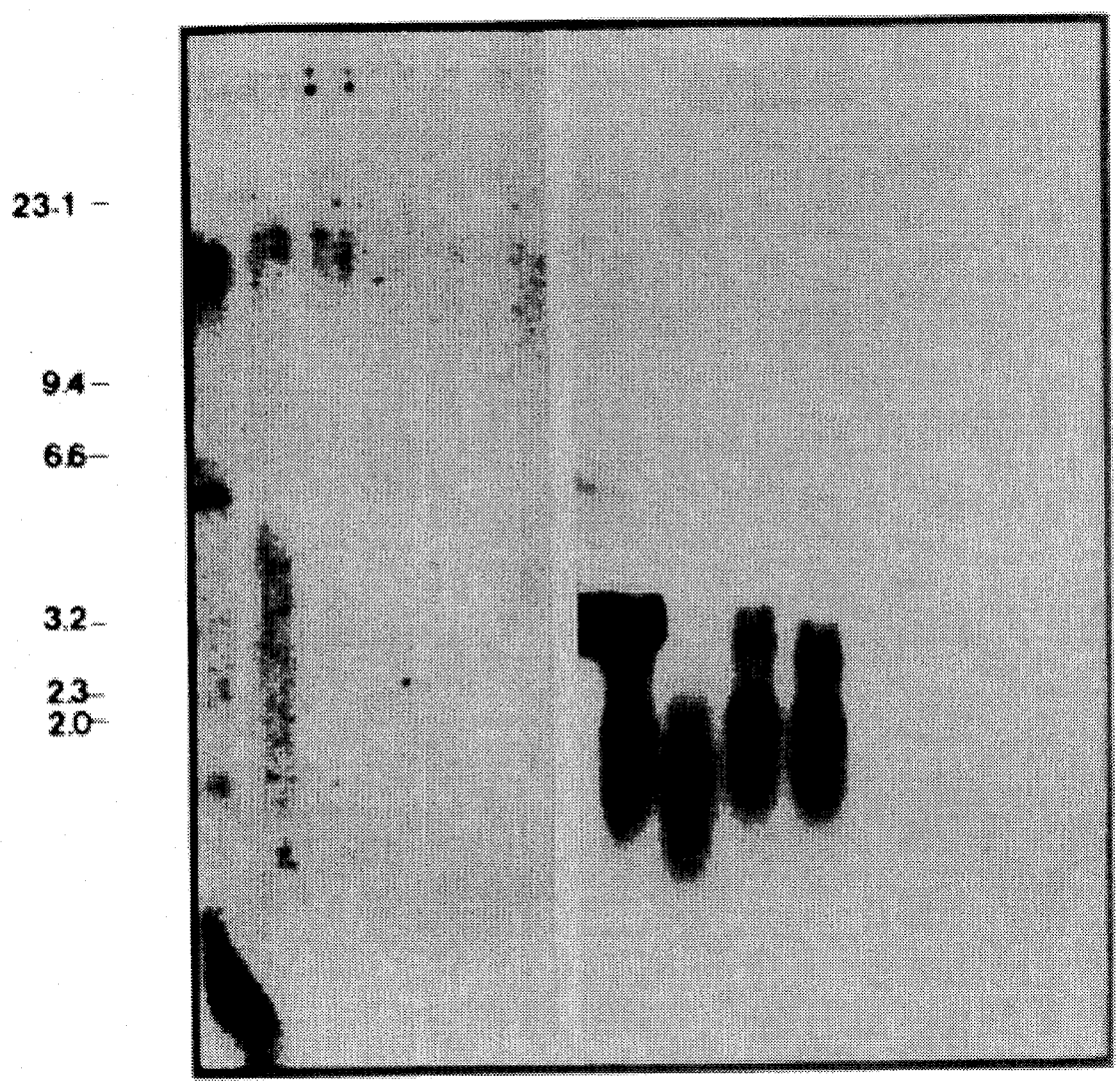

FIG. 9 is a photograph of a Southern blot analysis of human and chimpanzee restriction enzyme-cleaved liver DNAs from liver tissues that exhibited X protein, using hepatitis B virus (HBV) DNA as the binding probe. Total DNA was extracted from the cell powders made from the samples described in FIG. 8. Ten micrograms of DNA were loaded to each well of a 1% agarose gel. Restriction enzyme digestion buffers were according to manufacturer (BRL who, where). All digestions were carried out overnight at 37° C. with 50 units of enzyme (5 × DNA concentration in micrograms). Lanes 1–3 show chimp A-243 liver DNA digested with Bam HI, Eco RI or uncleaved, respectively; lanes 4–6 show chimp 344 liver DNA cleaved with Bam HI, Eco RI or uncleaved, respectively; lanes 7–10 show human HBcAg-positive liver DNA cut with Hind III, Bam HI, Eco RI or without digestion, respectively; and lanes 11–14 show human HBsAg-negative liver DNA digested with Hind III, Bam HI, Eco RI or undigested, respectively.

Figure 10:
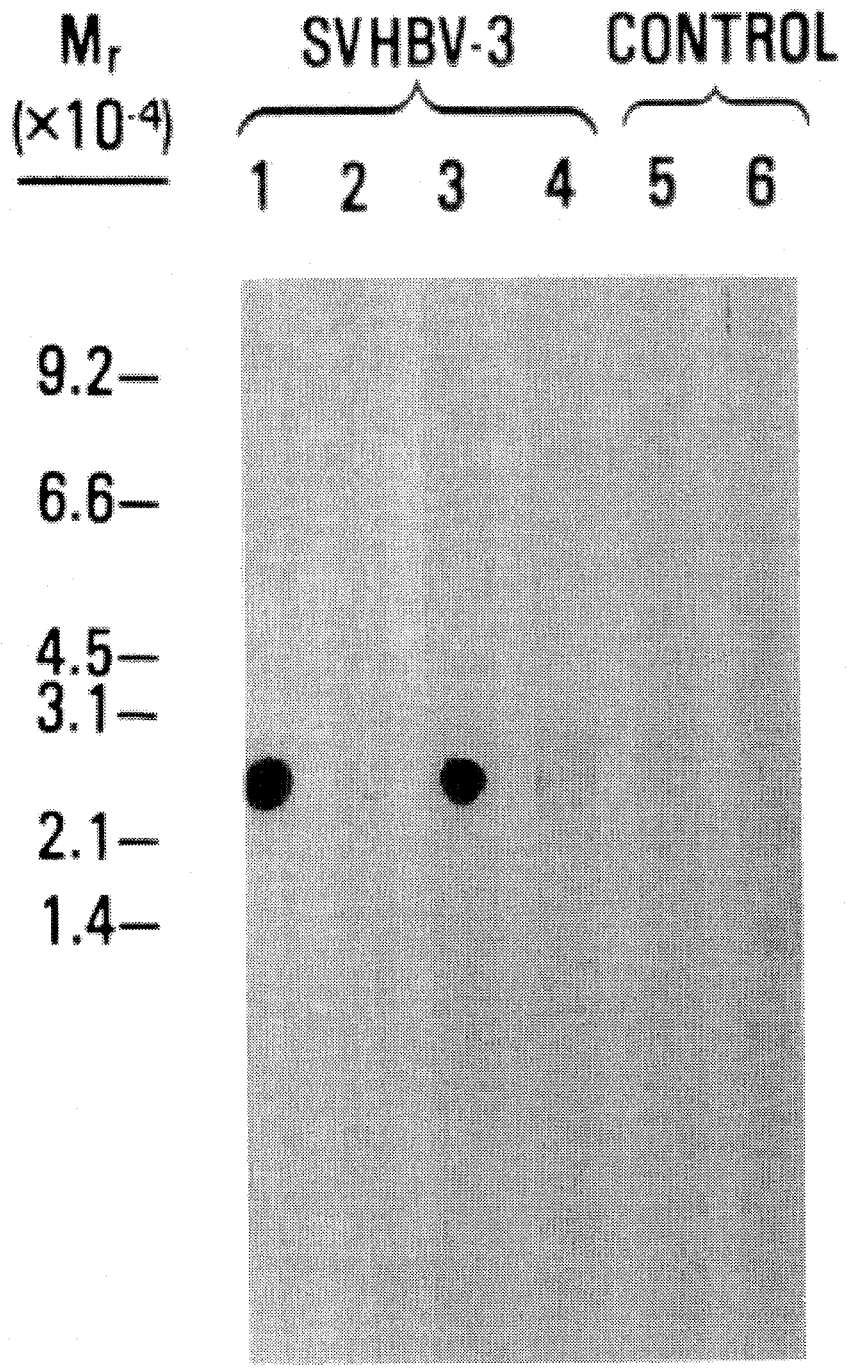

FIG. 10 is a photograph of an autoradiogram showing the reactivity of anti-X polypeptide antisera with an X-directed gene product. Confluent monolayers of BSC-1 cells ($2\times10^7$ cells) were infected with the recombinant SVHBV-3 stock virus (a mixture of $tsA_{239}$ and SVHBV-3 virions) or wild type SV40 (Moriarty et al. (1981), *Proc. Natl. Acad. Sci. USA*, 78: 2606–2610). The cultures were incubated in serum free DMEM at 40° C. for 48–72 hours at which time approximately 50% cytopathic effect had occurred. Supernatants were removed, and the flasks containing the monolayers were placed on ice for 5 minutes before the cells were collected by scraping. The collected cells were centrifuged, and the resulting cell pellets were washed with PBS, quick frozen at −70° C., and lyophilized overnight. The resultant cell powders were dissolved in PBS and brought to a final concentration of 2 mg/ml in sample buffer. The samples were boiled for 5 minutes, and cell debris was removed by centrifugation in a Beckman microfuge for 30 minutes. Fifty to one hundred micrograms of cell lysate was loaded onto denaturing polyacrylamide gels (12.5%) and subjected to electrophoresis as before-described. The proteins were electrophoretically transferred to nitrocellulose sheets as described previously. The nitrocellulose blots were stained in amido black prior to incubation at 4° C. overnight in BLOTTO for reduction of non-specific binding. Nitrocellulose strips were incubated for 3 hours at room temperature with a 1:350 dilution of anti-peptide antibodies in a final volume of 10 ml BLOTTO. The strips were washed in BLOTTO prior to a 1 hour incubation with $^{125}$I-labelled *S. aureus* protein A ($10^6$ cpm per 10 ml). The strips were washed as above, rinsed with water, dried and autoradiographed. In cases where blocking with polypeptide was performed, the antisera were preincubated with 100 micrograms of polypeptide solution overnight at 4° C. or 2 hours at 37° C. prior to incubation with the nitrocellulose strips. Molecular weights were based on low molecular weights standards (BioRad), and are shown at the left-hand margin of the Figure. Lanes 1 and 3 were reacted with anti-polypeptide 99 and anti-polypeptide 142 antibodies, respectively. Lanes 2 and 4 were reacted with those same antibodies preincubated with polypeptide 99 or with polypeptide 142, respectively. Lanes 5 and 6 show the reaction of anti-polypeptide 99 and 142 antibodies, respectively, with control cell lysates.

The instant invention has several benefits and advantages. One of those benefits is that for the first time, the presence of HBxAg in any cell has been detected.

Another benefit is that the invention provides an assay method and system for detecting the presence of HBxAg in a chronically hepatitis B-infected host animal.

Still another benefit is that use of the invention has enabled the detection of HBxAg in cells derived from human hepatomas, thereby strengthening the presumed link between hepatitis B virus and this form of cancer.

One of the advantages of the invention is that it provides means for cloning the gene coding for HBxAg. Another advantage of the invention is that it provides means for expressing a substantial polypeptide portion of HBxAg that may be used as an antigen in a diagnostic assay for the presence of antibodies to HBxAg (anti-X antibodies) that are present in the serum of humans.

Yet another advantage of the invention is the preparation of a synthetic polypeptide whose amino acid residue sequence corresponds to the sequence of an antigenic determinant of HBxAg that can be used to prepare antibodies that immunoreact with HBxAg as well as with polypeptides that share an antigenic determinant with HBxAg.

Still further benefits and advantages of the present invention will become apparent to those skilled in the art from the detailed description and claims that follow.

DETAILED DESCRIPTION OF THE INVENTION

Definitions

Transfection: is the acquisition of new genetic markers by incorporation of added DNA in eucaryotic cells.

Transformation: is the acquisition of new genetic markers by incorporation of added DNA in procaryotic cells.

Cloning vector: is any plasmid or virus into which a foreign DNA may be inserted to be cloned.

Plasmid: is an autonomous self-replicating extrachromosomal circular DNA.

Open Reading Frame: is a DNA sequence which is (potentially) translatable into protein.

Helper Virus: is a virus that provides functions absent from a defective virus, enabling the latter to complete the infective cycle during a mixed infection.

Gene (Cistron): is the segment of DNA that is involved in producing a polypeptide chain; it includes regions preceding and following the coding region (leader and trailer) as well as intervening sequences (introns) between individual coding segments (exons).

Expression: the process undergone by a structural gene to produce a polypeptide. It is a combination of transcription and translation.

Clone: describes a large number of identical cells or molecules with a single ancestral cell or molecule.

Base Pair (bp): is a partnership of adenine (A) with thymine (T), or of cytosine (C) with guanine (G) in a DNA double helix.

Expression Vector: is any plasmid or virus into which a foreign DNA may be inserted or expressed.

Downstream: identifies sequences proceeding farther in the direction of expression; for example, the polypeptide coding region for a gene is downstream from the initiation codon.

A. General Discussion

Region X of the hepatitis B virus HBV genome is of interest, inter alia, because recent evidence indicated the possibility of it being expressed and traditional HBV serology had not found its protein product or antibodies to such a product. Recently developed recombinant DNA and synthetic polypeptide technologies are used herein to overcome some of the failures encountered by traditional methodologies with respect to the expression of HBxAg, and to illustrate the expression of HBxAg in cells from human hepatoma-derived cell lines and in liver cells from chimpanzees and humans having a chronic HBV infection.

To that end, the present invention contemplates cloning and expression vectors for HBxAg, synthetic polypeptides that correspond to antigenic determinants of HBxAg and to antibodies raised to those synthetic polypeptides that bind to the polypeptides as well as to HBxAg, or to a substantial portion thereof, as well as assays for the presence of HBxAg.

The cloning vectors discussed herein are utilized, inter alia, for preparing useful quantities of an HBxAg-containing gene. That gene in turn may be used, inter alia, to prepare quantities of HBxAg and polypeptide fragments thereof that may be used in studying hepatitis B disease itself.

The novel synthetic polypeptides of this invention are useful, inter alia, as antigens in preparing antibodies that immunoreact with HBxAg and substantial polypeptide portions thereof, as well as immunoreacting with the synthetic polypeptides themselves. The antibodies so prepared may thereafter be utilized to assay for the presence of HBxAg or a substantial polypeptide portion thereof in the cells of an infected animal host or in tissue culture.

The expression vector may be used to transfect cells and induce expression of a polypeptide that includes a substantial portion of HBxAg. The expressed polypeptide may then be utilized as an antigen in an assay for determining the presence of antibodies to HBxAg in a body sample.

The expression vector and antibodies of this invention may also be used as a marker for transfected cells that contain the expression vector and further include an additional ligated gene whose presence may be relatively difficult to ascertain. Thus, the expression vector denominated SVHBV-3, described hereinafter, may be opened and ligated to still another, foreign gene that codes for a protein that may be relatively difficult to assay for. After recircularization, infection of suitable cells with the thus formed, new vector, and plating into single celled colonies, those cells that incorporated the new vector may be identified by their expression of the vector-encoded portion of HBxAg fused to the protein encoded by the foreign gene, using the antibodies of this invention. Such a marker can be particularly useful where the vector is desired to be expressed in eucaryotic cells; i.e., where drug resistance markers present in bacterial cell vectors such as pBR322 are not present.

1. Cloning Vectors

The recombinant DNA of the present invention, which contains the HBxAg gene can be produced, for example, by cloning a portion of the HBV DNA. To obtain HBV genomic material, Dane particle DNA containing a single stranded portion is converted to a completely double-stranded DNA by using the virus' endogenous DNA polymerase.

The circular, double-stranded HBV thus obtained contains two Bam HI endonuclease restriction sites. Cleavage with Bam HI typically yields three linear products classified by size. The largest is a 3200 base pair (bp) fragment representing the entire HBV genome cleaved at only one Bam HI site. Fragments containing 1850 bp and 1350 bp are produced when HBV is cleaved at both Bam HI sites.

Analysis of the HBV nucleotide sequence of Galibert et al. (1979), *Nature,* 281: 646–650, reveals that the 1850 bp HBV Bam HI fragment includes the gene coding for HBxAg. However, all three fragments have Bam HI complementary termini and may therefore be inserted into the Bam HI site of a cloning plasmid.

Figure 3:
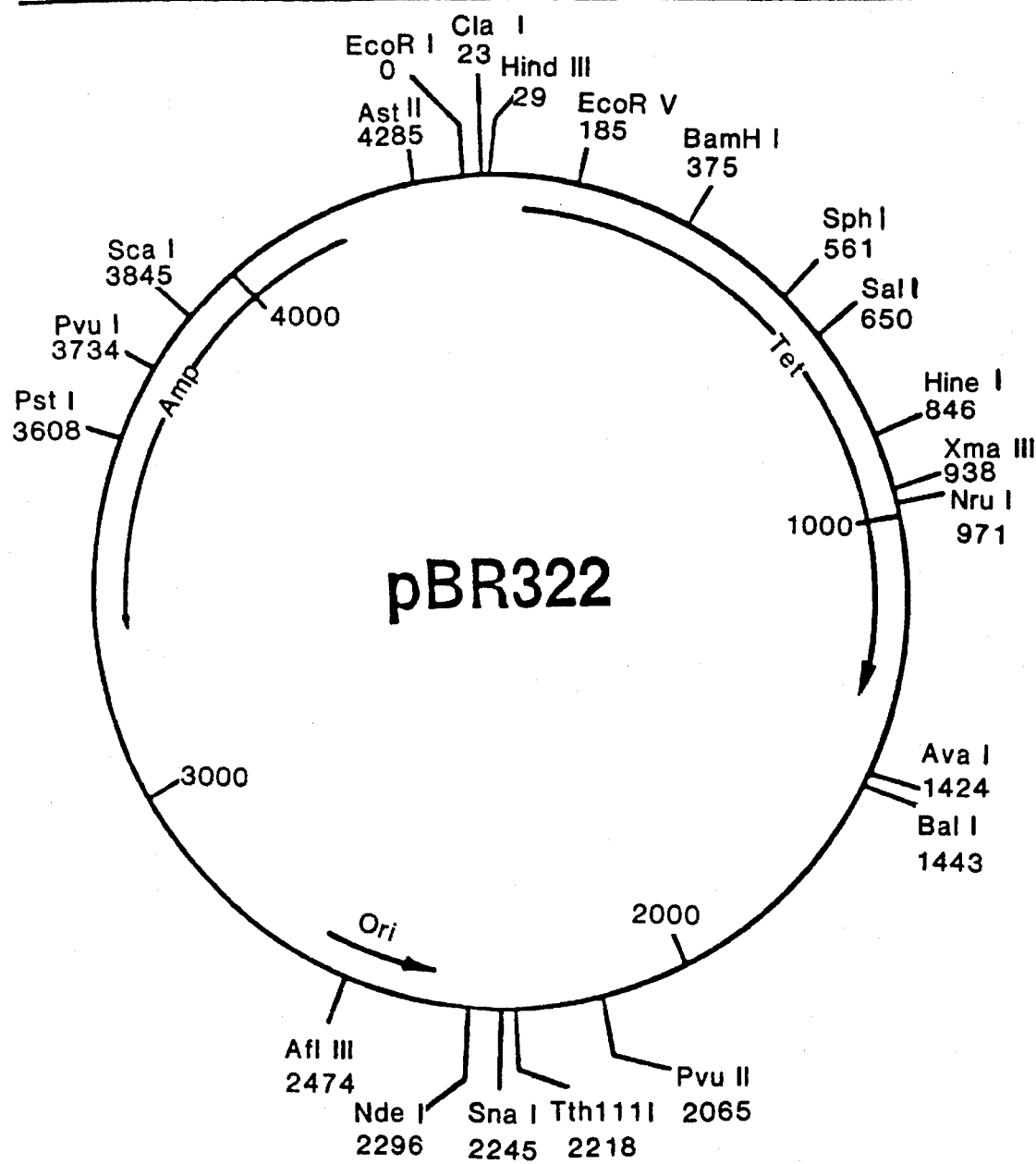
FIG. 3 schematically illustrates a plasmid pBR322 restriction map prepared from primary sequence data of Sutcliffe (1979), *Cold Spring Harbor Symposium on Quantitative Biology* 43, 77.

The plasmid pBR322 has a single Bam HI restriction site that is located within its tetracycline resistance-conferring gene as can be seen from examination of FIG. 3. Cleavage of pBR322 DNA with Bam HI yields a single linear fragment with termini complementary for each of the three Bam HI HBV DNA fragments.

Ligating each of the three Bam HI HBV DNA fragments into pBR322 at its Bam HI site with T4 DNA ligase to reform and circularize the plasmids resulted in three unique recombinant plasmid DNAs. The recombinant cloning plasmids are circular DNAs, and are designated: AM7, containing pBR322 DNA with the 1350 bp Bam HI HBV DNA fragment inserted at pBR322's Bam HI site; AM6, containing pBR322 DNA with the entire HBV genome inserted at pBR322's Bam HI site; and AM1, containing pBR322 DNA with the 1850 bp Bam HI HBV DNA fragment including the HBxAg gene inserted at pBR322's Bam HI site.

When the Bam HI HBV DNA fragments are ligated into the pBR322 Bam HI site with T4 DNA ligase, the recombinant plasmids so generated no longer have the ability to confer tetracycline resistance. Ampicillin resistant and tetracycline sensitive transformants were thereby selected from among colonies of the *Escherichia coli* (*E. coli*) strain HB101 transformed with the above ligation products.

Three drug selected strains of *E. coli* HB101 transformed with recombinant plasmids AM1, AM6 and AM7 are designated ECAM1, ECAM6 and ECAM7, respectively. The above plasmids were prepared in relatively large quantities by growing the above mentioned transformants in an appropriate medium such as LB broth, as described hereinafter.

From the above plasmids AM1 and AM6, a gene fragment containing the whole or part of the HBxAg gene base sequence may be excised by using appropriate restriction enzymes. For instance, when plasmids AM1 and AM6 were digested with the restriction enzyme Bam HI, an 1850 bp DNA fragment including the gene coding for HBxAg was isolated from the reaction products. By growing the recombinant plasmid-transformed *E. coli* HB101 strains ECAM6 or ECAM1, a relatively large amount of the DNA sequence coding for HBxAg can be obtained.

From the HBxAg gene for which the DNA base sequence and the locus on the HBV genome have been determined, it is evident that no introns exist therewithin. This means that the gene can be transcribed as it is to lead to phenotypic expression as a messenger RNA in animal cells as well as in bacterial cells.

2. Expression Vectors

Introduction of the HBxAg gene with an appropriate expression system into an animal cell, for example, an African Green Monkey kidney cell by the method of Ganem et al. (1976), *J. Mol. Biol.,* 101: 57–83, can lead to HBxAg synthesis within said cell. Furthermore, cultivation of those monkey kidney cells containing the HBxAg gene with an appropriate expression vector enables low-cost mass production of HBxAg.

Advantageously, a recombinant DNA capable of expressing the HBxAg gene was constructed by inserting, without shifting its reading frame, the complete HBxAg gene, or a fragment thereof, into the Simian Virus 40 (SV40) downstream from the SV40 late region promoter. A vector for expression using the SV40 late region promoter was produced in large quantities in the following manner.

SV40 DNA and pBR322 DNA were subjected to Bam HI and Eco RI double restriction enzyme digestion. The larger SV40 and pBR322 fragments were ligated using T4 DNA ligase. The ligation product was subjected to Bam HI digestion forming a linear DNA with Bam HI cohesive termini. Ligation of this SV40/pBR322 DNA with the 1850 bp Bam HI HBV DNA resulted in a circular recombinant plasmid denominated SVAM191.

The recombinant DNA SVAM191 contains an intact *E. coli* ampicillin resistance gene. *E. coli* HB101 transformed with SVAM191 are ampicillin resistant and tetracycline sensitive, and thus may be selected for based on drug sensitivity. *E. coli* HB101 transformed with SVAM191 are designated EC-SVAM191, and may be grown in an appropriate medium, such as LB broth containing ampicillin, and a relatively large amount of said plasmid may thereby be obtained.

3. Cell Culture

The transformation of a host cell with the thus-obtained recombinant DNA plasmids AM1, AM6 and SVAM191 can be conducted by known methods (Cohen et al., *Proc. Natl. Acad. Sci. USA,* 69:2110–2114 (1972)) or a modification thereof. The host cells include, among others, such microorganisms as *Escherichia coli* (*E. coli*), *Bacillus subtilis* and yeasts, and preferably are an *E. coli* strain such as the strains denominated 294 (ATCC 31446), W3110 (ATCC 27325) or RR1 (ATCC 31447). *E. coli* strain HB101 (ATCC 33694) is a particularly preferred host cell line.

Isolating a cell strain carrying the HBxAg gene-containing novel recombinant plasmid DNA may be accomplished by known methods including, for instance, the following technique.

Dane particle DNA which is only partially double-stranded may be radioactively labeled by filling in the single-stranded portion with $^3$H-containing dNTPs using the endogenous DNA polymerase reaction. Robinson (1975), *Am. J. Med. Sci.,* 270: 151–159. Thereafter, using the labeled product as a probe, a positive clone can be picked out from among the already-obtained drug-selected transformants by the known Southern Blot Hybridization method (Southern (1975), *J. Mol. Biol.,* 98: 503), or by the known colony hybridization method (Grunstein et al. (1975), *Proc. Natl. Acad. Sci. USA,* 72: 3961–3965).

Host cells transformed and isolated in this manner are grown in a known medium. The medium may be, for instance, LB broth, Penassay broth, or M9 medium containing glucose and cis amino acids (Miller, *Experiments in Molecular Genetics,* 431–433 (Cold Spring Harbor Laboratory, New York, 1972)).

The cultivation is generally carried out at 15°–43° C., preferably at 28° C.–40° C., for 2–24 hours, preferably for 4–16 hours, if necessary with aeration and/or agitation.

After the cultivation, the bacterial cells are collected, the cells are suspended in a buffer and lysed, as by lysozyme, freeze-thawing or ultrasonic treatment. The gene coding for HBxAg may be isolated by a method generally known for DNA purification from the centrifugation supernatant obtained following cell lysis.

To produce a vector for expressing HBxAg in eucaryotic cells, a portion of the SVAM191 DNA, including all the DNA of pBR322 origin, was removed. This was accomplished by subjecting SVAM191 to Hae II restriction enzyme digestion. When the larger of the Hae II SVAM191 digestion products was circularized, a vector capable of expressing HBxAg in animal cells, designated SVHBV-3, was formed.

A mammalian cell host may be transfected with SVHBV-3 by known methods to provide an expression system. For instance, SVHBV-3 when cleaved with the restriction enzyme Hind III may be inserted into COS-7 cells (ATCC CRL 1651). (See, Gluzman (1981), *Cell,* 23: 175–182; and Siddiqui (1983), *Mol. and Cell Biology* 3: 143–146.) SVHBV-3 may also be inserted in Bovine Papilloma Virus and thereby used to transfect murine cell lines.

More preferably, SVHBV-3 is used along with SV40tsA$_{239}$ helper virus to transfect the African Green Monkey kidney cell line BSC-1 (ATCC CCL 26). When so transfected, BSC-1 cells produced a polypeptide containing HBxAg antigenic determinants.

It should be understood that the nucleotide sequence or gene fragment inserted at the selected restriction site of the cloning or expression vehicle may include nucleotides that are not part of the actual gene for the desired protein or may include only a fragment of that gene. Thus, because of the known redundancies in the genetic code, the inserted gene need not be identical to the HBxAg gene described herein, but need only code for HBxAg. In addition, a DNA sequence that codes for HBxAg may include additional bases at either or both of the 3'- or 5'-ends of the sequence that codes for HBxAg, so long as the reading frame is unchanged. Put differently, whatever DNA sequence is inserted, the present invention requires only that the transformed or transfected host produce either a DNA coding for HBxAg, the protein HBxAg, or a polypeptide that includes a substantial portion of the HBxAg protein, respectively.

4. Polypeptides, Antigens and Antibodies

As described hereinafter, the expression of HBxAg can be detected using antibodies induced by synthetic polypeptides whose amino acid residue sequence corresponds to the amino acid residue sequence of an antigenic determinant of HBxAg. The polypeptides of this invention typically contain about 6 to about 40 amino acid residues. More preferably, those polypeptides contain about 10 to about 20 amino acid residues.

The amino acid residue sequence of synthetic polypeptides designated 8, 42, 79, 99, and 100 and 142 shown below and in FIG. 6 were determined from the HBV nucleotide sequence as published by Galibert et al., supra.

Polypeptide 8: Gln-Leu-Asp-Pro-Ala-Arg-Asp-Val-Leu-Cys-Leu-Arg-Pro-Val-Gly,

Polypeptide 42: Ser-Ala-Val-Pro-Thr-Asp-His-Gly-Ala-His-Leu-Ser-Leu-Arg-Gly-Leu-Pro-Val-Cys, Polypeptide 79: Met-Glu-Thr-Thr-Val-Asn-Ala-His-Gln-Ile-Leu-Pro-Lys-Val-Leu-His-Lys-Arg-Thr-Leu-Gly, Polypeptide 99: Leu-Ser-Ala-Met-Ser-Thr-Thr-Asp-Leu-Glu-Ala-Tyr-Phe-Lys-Asp-Cys, Polypeptide 100: Cys-Leu-Phe-Lys-Asp-Trp-Glu-Glu-Leu-Gly-Glu-Glu-Ile-Arg-Leu-Lys-Val, and Polypeptide 142: Ala-Pro-Ala-Pro-Cys-Asn-Phe-Phe-Thr-Ser-Ala, wherein each of the amino acid residue sequences is shown in the direction from left to right and in the direction from amino-terminus to carboxy-terminus.

It is noted that polypeptides corresponding in amino acid residue sequence to the sequences of polypeptides 99 and 100 except for the absence of the carboxy- and amino-terminal cysteine residues of polypeptides 99 and 100, respectively, are also useful herein and are considered a part of this invention. Such polypeptides designated polypeptides 99b and 100b are useful as immunogens when bound to a carrier through their amino- or carboxy-terminal residues and may also be used in immunoreaction blocking studies similar to those shown in portions of FIGS. 7, 8, and 10 and discussed hereafter.

The amino acid residue sequences of polypeptides 99b and 100b are shown in the formulae below from left to right and in the direction from amino-terminus to carboxy-terminus:

Polypeptide 99b: Leu-Ser-Ala-Met-Ser-Thr-Thr-Asp-Leu-Glu-Ala-Tyr-Phe-Lys-Asp,

Polypeptide 100b: Leu-Phe-Lys-Asp-Trp-Glu-Glu-Leu-Gly-Glu-Glu-Ile-Arg-Leu-Lys-Val.

a. X Protein in Transfected Cells

Rabbits immunized with polypeptides 99, 100 or 142 linked to a keyhole limpet hemocyanin (KLH) carrier as a conjugate produced antibodies (anti-99, anti-100, and anti-142,respectively) that immunoreacted with the HBxAg polypeptide expressed in BSC-1 cells transfected with SVHBV-3, thereby demonstrating for the first time the expression of an HBxAg polypeptide in those or any cells. Those anti-polypeptide antibodies did not immunoreact with any polypeptide found in non-transfected BSC-1 cells; i.e., cells infected with wild type (wt) SV40.

In addition, the immunoreactivity of the anti-polypeptide antibodies which expressed the HBxAg polypeptide was inhibited or blocked by pre-incubation of the antibodies with their complementary (corresponding) polypeptide; i.e., the polypeptide immunogen to which they were raised. That blocking indicates that the antibodies specifically recognized an antigenic determinant of the polypeptide predicted to be HBxAg, and that the synthetic polypeptides corresponded in amino acid residue sequence to antigen determinants of the predicted HBxAg protein. These blocking results were obtained using the Western Blot technique (Materials and Methods) followed by the location of bound antibodies with $^{125}$I-labeled S. aureus protein A, followed by autoradiographic development of the assay.

These results are shown in FIG. 10 for antisera to polypeptides 99 and 142. Lane 1 of FIG. 10 shows the immunoreaction of anti-99 with the SVHBV- 3 infected cell lysate, while lane 2 shows blockage of that immunoreaction by pre-incubation of the antiserum with polypeptide 99. Similarly, anti-142 immunoreacted with a cell lysate protein in lane 3, and that immunoreaction was blocked by pre-incubation of that antiserum with polypeptide 142. Lanes 5 and 6 show that no immunoreaction took place with lysates from control cells.

The polypeptide expression product of SVHBV-3 transfected cells that was specifically identified by antisera to polypeptides 99 and 142, as shown in FIG. 10, had a molecular weight of about 24,000 daltons. As discussed below, a polypeptide having a molecular weight of about 28,000 daltons has been identified in lysates from the human hepatoma-derived cell line PLC/PRF/5. It is believed that the molecular weight difference in the polypeptides (proteins) expressed by the two cell lines stems from the fact that the polypeptides expressed result from fusion of the X protein with other proteins or polypeptides.

Thus, as already noted, SVHBV-3 lacks a portion of the complete X-encoding genome. FIG. 6 shows that the portion of the X gene included in SVBHV-3 excludes codons for the first twenty-two amino acid residues of the putative X protein including the methionine initiation codon ATG.

It was therefore predicted that the polypeptide expressed by cells transfected by SVHBV-3 would be a fusion product with the SV40 structural protein VP2 sequences present in the vector. The predicted size of the fusion protein (polypeptide) was predicted to be 24,500 daltons. The finding of an expressed polypeptide having a molecular weight of about 24,000 daltons thereby conforms to that prediction. The 28,000 dalton fusion protein (polypeptide) is discussed hereinafter.

b. X Protein Expressed in Hepatoma Cells

Expression of BHxAg is also believed to be a function of some HBV disease states. For example, antibodies to polypeptide 99 (anti-99) specifically recognized a 28,000 dalton protein expressed in the human hepatoma-derived cell line PLC/PRF/5 (ATCC CRL 8024). Normal rabbit serum did not recognize this protein and anti-99 recognition was blocked by pre-incubation with polypeptide 99. This cell line is known to contain integrated HBV DNA. Chakrabarty et al. (1980), Nature, 286: 531–533; Edman et al. (1980), Nature, 286: 535–538; and Marion et al. (1980), Virol, 33: 795–806. HBsAg has been detected in this hepatoma cell line, (McNab et al. (1976), Cancer, 34: 509–515; and Aden et al. (1979), Nature, 282: 615–616), while all standard assays for HBcAg and HBeAg have been negative. The cell line denominated HepG2 (ATCC CCL 23) is also a human hepatoma cell line, but does not contain integrated HBV DNA sequences. Aden et al., supra.

These results were obtained by radiolabeling the PLC/PRF/5 cell proteins followed by repeated immunoprecipitations using anti-99 and S. aureus protein A and then electrophoresis of the recovered precipitate. The 28,000 dalton protein was then identified by autoradiography. This procedure is also discussed in the Materials and Methods section.

Results from a similar study using lysates from both PLC/PRF/5 and HepG2 cells are shown in FIG. 7. FIG. 7 demonstrates that an X-specific protein at 28,000 daltons was detected in PLC/PRF/5 cells (lane 5). The immunoreactivity was lost when antibody was preincubated with polypeptide 99 (lane 6), but not with a non-related polypeptide (lane 7). The preimmune serum control did not immunoreact (lane 8). No X-specific reactivity was detected in the control HepG2 lysates (lanes 1–4). These results establish that an X gene product is being expressed in a human hepatoma cell line containing integrated HBV DNA sequences.

c. X Protein Expression in Liver Cells

In addition, four liver samples from human and chimpanzee, either with or without a history of HBV infection, were examined in a Western blot assay for the presence of an X related protein using anti-X polypeptide antibodies. The results of this examination are shown in FIG. 8. One human sample (H) was from a chronically HBV infected hepatoma liver and the other from an acute phase HBV infection (H). An uninfected chimpanzee (C) and one chronically infected with HBV (C) were both used to obtain liver cell lysates that were reacted against anti-X polypeptide antibodies.

Anti-99 antibodies reacted against both a 45,000 and 28,000 (left-margin arrow, right-margin p28) dalton protein. Both reactivities were blocked when these antibodies were preincubated with polypeptide 99. When anti-142 antibodies were reacted against these same cell lysates, specific bands at 40,000 (p40), 28,000 (p28) and 17,000 (p17) were detected. The reactivities against these proteins are considered specific because they are removed when anti-142 antibodies are preincubated with polypeptide 142.

The control sample, an uninfected chimpanzee liver (lane 3 of all panels), exhibited the about 45,000 dalton protein (p45) with anti-99 antibodies and both p40 and p17 with anti-142 antibodies. Protein p28 was expressed in HBV infected tissues only (lanes cells (lane 5). The immunoreactivity was lost when antibody was preincubated with polypeptide 99 (lane 6), but not with a non-related polypeptide (lane 7). The preimmune serum control did not immunoreact (lane 8). No X-specific reactivity was detected in the control HepG2 lysates (lanes 1–4). These results establish that an X gene product is being expressed in a human hepatoma cell line containing integrated HBV DNA sequences.

The presence of a 45,000 dalton protein was also observed in a relatively small amount in the lysates from PLC/PRF/5 cells shown in FIG. 7. The immunoreaction between anti-99 antibodies and the 45,000 dalton protein was also blocked by pre-incubation of the antibodies with the immunizing polypeptide 99. This is shown in lane 6 of FIG. 7.

Normal human liver cell extracts (HBV seronegative) were found to express only the 45,000 dalton protein in the Western Blot assay using anti-99. In addition, control assays run using commercially available antibodies raised to HBs, HBc and HBe (Abbott Laboratories, North Chicago, Ill.) failed to identify either protein located by the antibodies of this invention. This evidence again suggests that the 45,000 dalton protein has antigenic determinants homologous with HBxAg, but that the 28,000 dalton protein recognized by anti-99 is specific for a HBV disease state, and is different from HBsAg, HBeAg and HBcAg.

d. X Gene in Liver Cells

The expression of p28 in PLC/PRF/5 cells was from HBV DNA integrated into the host DNA. It was of interest to determine if this were the only way in which X protein could be expressed.

Therefore, those chimpanzee and human liver DNAs that exhibited X protein were probed with HBV DNA (FIG. 9). Total DNA was isolated from the liver tissues represented in FIG. 9; and were analyzed for the presence of HBV-DNA sequences. The DNA from the 28,000 dalton protein-containing chimpanzee revealed homologous bands when cleaved with Bam HI, Eco RI or when undigested (FIG. 9, lanes 1, 2 and 3 respectively). Bam HI cleaves circular HBV DNA into two fragments (1850 and 1350 base pairs (bp)), the band at 5.8 kilobases (Kb) (lane 1) represents a larger than genome size integrated sequence. Since no bands were seen below the high molecular weight DNA band (lane 3) it is concluded that only integrated sequences of HBV are present in this DNA.

In addition, DNA from an HBcAg-positive human liver was prepared, and was probed with HBV DNA. Restriction enzyme cleavage with Hind III, Bam HI, Eco RI or undigested DNA (FIG. 9, lanes 7–10, respectively) revealed homologous sequences either equal to or smaller than genome size, thereby eliminating any evidence that these human DNA samples contain integrated sequences. Chimp and human liver tissues lacking the 28,000 dalton protein were also negative for HBV DNA sequences (FIG. 9, lanes 4–6 and 11–14, respectively). The data shown in FIG. 9 confirm that X protein is expressed in HBV infected tissues regardless of the state of the HBV genome, and therefore eliminate a prerequisite of HBV DNA integration for X expression.

e. Summary of Results

The results described hereinbefore demonstrate the existence of a previously unidentified viral-encoded protein in HBV infected human and chimpanzee liver tissues. This 28,000 dalton protein (p28) is encoded by the HBV genome whether it exists free in an extrachromosomal form or is found integrated into the cellular DNA.

The 28,000 dalton protein (p28) is not the product of the X region alone, but contains additional HBV sequences. The predicted size of X protein, based on the sequence reported by Galibert et al. supra, is about 17,000 daltons (FIG. 6)). However, the molecular weight of the X protein detected by anti-X peptide antibodies in PLC/PRF/5 cells, as well as in chimpanzee and human HBV- infected tissues is 28,000 daltons. The discrepancy in size is not due to a fusion of the X gene with cellular sequences since the lack of integrated HBV DNA in human tissues expressing p28 (FIG. 9, lanes 7–10) indicates that the X protein (p28) is translated solely from the HBV genome.

The increased size of the X protein can be explained if the protein is either an HBsAg-X or an X-HBcAg fusion. The probability of such a fusion is suggested by the proximity of these HBV genes to one another on the genome.

An attempt to determine the existence of such a fusion on the RNA level was unsuccessful, due to the fact that the transcripts obtained in the PLC/PRF/5 cells, which were found to contain X sequences, were also exhibiting either surface or core sequences as well as X (data not shown). Similar results were reported by Gough (1983), *J. Mol. Biol.*, 165: 683–699. Evidence for an X-core fusion comes from the DNA sequence of another member of the Hepadnavirus family, the duck hepatitis B virus (DHBV), where both genes are translated as a single protein (Mandart, et al. (1984), *J. Virol.*, 49: 782–792) and from work by Feitelson et al. (1982), *J. Virol.*, 43: 687–696.

The fact that the X region of HBV is expressed has been established. However the function of this gene product remains unknown. A protein molecule, which has been suggested to be the translation product of the X region, is found in association with the HBV genome, or more specifically, is covalently linked to the 5' nick of the L strand Gerlich et al. (1980), *Cell*, 21: 801–809. The idea of X protein representing a DNA binding protein was eliminated when DNAase treatment of PLC/PRF/5 cells or HBV infected tissues failed to remove or alter p28 activity (data not shown).

Presently, little is known concerning the biology of HBV infection, or the correlation made between HBV infection and the subsequent onset of hepatocellular carcinoma. To this end, any additional marker for HBV infection or for the presence of HBV sequences is of major importance. Human sera are presently being examined for the existence of anti-X antibodies and the X protein.

The term "correspond" in its various grammatical forms is used herein and in the claims in relation to polypeptide sequences to mean the polypeptide sequence described plus or minus up to three amino acid residues at either or both of the amino- and carboxy-termini and containing only conservative substitutions in particular amino acid residues along the polypeptide sequence.

The term "conservative substitution" as used above is meant to denote that one amino acid residue has been replaced by another, biologically similar residue. Examples of conservative substitutions include the substitution of one hydrophobic residue such as Ile, Val, Leu or Met for another, or the substitution of one polar residue for another such as between Arg and Lys, between Glu and Asp or between Gln and Asn, and the like.

in some instances, the replacement of an ionic residue by an oppositely charged ionic residue such as Asp by Lys has been termed conservative in the art in that those ionic groups are thought to merely provide solubility assistance. In general, however, since the replacements discussed herein are on relatively short synthetic polypeptide antigens, as compared to a whole protein, replacement of an ionic residue by another ionic residue of opposite charge is considered herein to be a "radical replacement", as are replacements between nonionic and ionic residues, and bulky residues such as Phe, Tyr or Trp and less bulky residues such as Gly, Ile and Val.

The terms "nonionic" and "ionic" residues are used herein in their usual sense to designate those amino acid residues that normally either bear no charge or normally bear a charge, respectively, at physiological pH values. Exemplary nonionic residues include Thr and Gln, while exemplary ionic residues include Arg and Asp.

The word "antigen" has been used historically to designate an entity that is bound by an antibody, and also to designate the entity that induces the production of the antibody. More current usage limits the meaning of antigen to that entity bound by an antibody, while the word "immunogen" is used for the entity that induces antibody production. In some instances, the antigen and immunogen are the same entity as where a synthetic polypeptide is utilized to induce production of antibodies that bind to the polypeptide. However, the same polypeptides (99, 100 or 142) also induce antibodies that bind to a whole protein such as HBxAg, in which case the polypeptide is both immunogen and antigen, while the HBxAg is an antigen. Where an entity discussed herein is both immunogenic and antigenic, it will generally be termed an antigen.

5. Assay Systems and Methods

The above results indicate that SVHBV-3 may be used as an expression vector. It provides expression control elements for foreign DNA sequences inserted in reading frame downstream from the HBxAg gene.

The results also indicate that synthetic polypeptides 99, 100 and 142, and antipeptide antibodies thereto may be used as part of an assay system and method for detecting the presence of HBxAg in a body sample to be assayed such as hepatoma cells or liver cells from an animal host suspected of having HBxAg, to detect successful transfection with SVHBV-3, and to monitor expression when SVHBV-3 is used as an expression vector.

Such a system includes at least a first reagent containing receptor molecules that include an antibody combining site such as antibodies, substantially whole antibodies or the well known Fab and $F(ab')_2$ antibody portions, and are capable of immunoreacting with a synthetic polypeptide of this invention; i.e., raised to the synthetic polypeptides of this invention. Indicating means, such as a fluorescent dye like fluorescein or rhodamine, a radioactive element like iodine-125 or carbon-14, or an enzyme-linked antibody raised to the first reagent's receptors (e.g. peroxidase-linked goat anti-rabbit IgG), to signal immunoreaction of the receptors of the first reagent with the expression specific HBxAg are also provided. The indicating means may be initially bound or free from the first reagent. Typical uses of such a HBxAg assay reagent system include enzyme-linked immunosorbent assays (ELISA), radioimmunoassays and immunofluorescent assays (IF).

Diagnostic assays for determining the presence of HBxAg in a body sample utilizing the polypeptides of this invention and their anti-polypeptide antibodies have already been broadly described. In a commercial embodiment of such a diagnostic assay, a diagnostic assay system is contemplated.

One such system includes provision of at least one container having an anti-polypeptide receptor such as anti-8, -42, -79, -99 or -142 as the first reagent. A second container having a quantity of the polypeptide to which the anti-polypeptide antibody was raised, e.g. polypeptide 8, 42, 79, 99 or 142, may also be supplied to provide a second reagent. Additional containers having the before-described indicating means, one or more buffers, and the like as are well known may also be provided to the diagnostic assay system.

A method for assaying for the presence of a detectable amount of HBxAg has also been broadly described hereinbefore. Briefly, that method includes admixing proteins from a body sample to be assayed such as hepatoma or liver cells with receptors that include an antibody combining site capable of immunoreacting with a synthetic polypeptide of this invention and with HBxAg, such as anti-S, -42, -79,- 99, or -142, or an Fab or F(ab') portion thereof, in the presence of an indicating means such as $^{125}$I-labeled *Staphylococcus aureus* (*S. aureus*) protein A or an enzyme label, like horseradish peroxidase linked to one of the above receptors for signalling an immunoreaction between HBxAg and the receptors. The admixture is maintained for a time period sufficient for the indicating means to signal that an immunoreaction has occurred, and the presence of the signal is ascertained as by an autoradiogram. The body sample, or the proteins therefrom, is preferably adsorbed or otherwise affixed (bound) to a solid matrix such as a nitrocellulose sheet or glass slide prior to being admixed with the receptors.

Where the indicating means is a separate molecule such as radiolabeled *S. aureus* protein A, the bound body sample and receptor molecules are admixed first, in the absence of the indicating means, and the admixture is maintained for a time period sufficient to form a bound immunoreaction product. The bound immunoreaction product is then rinsed. The separate molecule indicating means is then admixed with the bound immunoreaction product, and that admixture is maintained for a time period sufficient for a bound, second reaction product to form. The bound second reaction product is then rinsed, and the presence of a signal from the indicating means is determined.

Where the indicating means is a portion of the receptors of this invention, those labeled receptors are admixed with the bound body sample to be assayed, and the admixture is maintained for a time period sufficient for an immunoreaction product to form. The bound immunoreaction product is then rinsed, and the presence of a signal from the indicating means is determined.

The before-mentioned second reagent, e.g., polypeptides 8, 42, 79, 99 or 142, may be used as a control reagent in an immunoreaction blocking study to verify that specific, rather than non-specific, immunobinding has occurred. Such blocking studies are illustrated in FIGS. 7, 8 and 10.

To use SVHBV-3 as an expression vector, foreign DNA is inserted downstream from the HBxAg gene, preferably at its unique Bam HI restriction site, and the new vector so produced is utilized to transfect cells. Expression of HBxAg in a transfected cell is presumptive evidence of expression of the foreign DNA inserted into SVHBV-3. Expression of HBxAg detected by the above described HBxAg expression assay system indicates the expression of foreign DNA inserted into SVHBV-3.

Thus, examination of cell colonies produced after the attempted transfection using the above assay system can be utilized to select those colonies in which transfection was successful. For example, cells from colonies resulting from the attempted introduction of the vector into eucaryotic cells are harvested, lysed, and the cellular proteins are extracted. The extracted cellular proteins are thereafter separated on a SDS-polyacrylamide gel by electrophoresis, and the separated proteins are blotted onto nitrocellulose. Contacting the blotted proteins with an excess of receptor and label of the before-described assay system such as $^{125}$I-labeled antibodies to synthetic polypeptide 99 or polypeptide 142, followed by rinsing to remove the non-immunoreacted antibodies (receptors) can then be used to prepare an autoradiograph that indicates the presence of the expressed HBxAg portion that is fused to the polypeptide encoded by the foreign gene.

The before described assay methods and systems are particularly useful for identifying the X protein or a substantial portion thereof that may be present in a body sample, particularly a tissue sample such as in cells from a liver biopsy. The diagnostic assay and method described hereinbelow is particularly useful for determining the presence of antibodies to the X protein that may be present in a body sample such as whole blood, serum or plasma. A Western blot analysis will be used as exemplary of such a diagnostic method. However, a commercial embodiment that utilizes the method is an ELISA (enzyme-linked immunosorbant assay) diagnostic system.

Here, an expression product from SVHBV-3 vector-transfected cells such as the approximately 24,000 dalton protein (polypeptide) expressed in BSC-1 cells discussed in relation to FIG. 10 is preferably utilized as the antigen, although a preferred polypeptide of this invention such as polypeptide 99 or polypeptide 142 may also be used as an antigen. Thus, the HBxAg molecule itself, used in substantially purified form as obtained by affinity chromatography as discussed hereinafter, a substantial portion of the HBxAg molecule such as is expressed by SVHBV-3 transfected BSC-1 cells (the 24,000 dalton polypeptide), or a polypeptide corresponding in amino acid residue sequence to an antigenic determinant of HBxAg may be used as the antigen.

The antigen is preferably bound on (adsorbed to) or otherwise affixed to a solid matrix such as the cross-linked dextran available under the trademark SEPHADEX from Pharmacia Fine Chemicals (Piscataway, N.J.), agarose, beads of glass, polyvinyl chloride, polystyrene, cross-linked acrylamide, nitrocellulose or the wells of a microtiter plate to form a solid support. The antigen, preferably bound to a solid matrix as part of a solid support, is admixed with a liquid body sample to be assayed to form a solid-liquid phase admixture. The admixture is maintained for a time period sufficient for anti-X protein (anti-HBxAg) antibodies (HBxAb) present in the body sample to immunoreact with the antigen. The presence of that immunoreaction is then determined as with an indicating means to signal the presence of anti-X protein antibodies in the assayed body sample.

For example, in one study, SVHBV-3 vector-transfected BSC-1 cell lysates were prepared, separated electrophoretically, and were transferred and bound to nitrocellulose sheets as a solid matrix in a manner substantially similar to that discussed in relation to FIG. 10 to form a solid phase. Sera diluted 1:50 from six patients with various hepatic diseases were then separately admixed with the nitrocellulose-bound transfected BSC-I cell proteins to form solid-liquid phase admixtures. Those admixtures were maintained for a time period (2 hours) sufficient for anti-X antibodies present in the sera to immunoreact with the bound antigen.

After rinsing to separate the solid and liquid phases, the solid phases resulting from the above steps were separately admixed with liquid solutions containing 1:200 dilutions of goat anti-human or anti-rabbit antibodies conjugated to horseradish peroxidase as an indicating means to form second, solid-liquid phase admixtures. The separate, second, solid-liquid phase admixtures were maintained for a time period (1 hour) sufficient for the labeled antibodies to react with human anti-X antibodies that had immunoreacted with the matrix-bound antigen. Rabbit anti-polypeptide antibodies were used as controls with the goat anti-rabbit antibodies. The resulting solid-liquid phases admixture were again separated and rinsed. The resulting solid phases were then using solutions containing 4-chloro-1-naphthol as described for FIG. 8.

The results of this study indicate that serum from a patient diagnosed as having a hepatocellular carcinoma contained antibodies that bound to the polypeptide expressed by the SVHBV-3 vector in the transfected BSC-1 cells. Those antibodies are thus anti-X antibodies, and their presence establishes the X gene product as an authentic antigen at some stage of HBV infection.

Where the approximately 24,000 dalton polypeptide expression product used in the above-described Western blot assay is utilized as the antigen in an ELISA, as discussed hereinbelow, or in other similar assays, that polypeptide is preferably purified and isolated prior to such use. That purification and isolation may be achieved by well known techniques.

For example, anti-8, -42, -79, -99, or -142 antibodies, or the antibody combining sites thereof, may be prepared as described herein and linked to a solid matrix such as the agarose and cross-linked agarose derivatives sold under the trademarks SEPHAROSE 6B, CL6B, 4B and CL4B by Pharmacia Fine Chemicals or those sold under the trademarks Bio-Gel A-0.5M, A-1.5M, and A-50M by Bio-Rad Laboratories of Richmond Calif. The before-described cross-linked dextran sold under the trademark SEPHADEX, and polyacrylamide beads sold under the trademarks Bio-Gel P-2, P-30, P-100 and P-300 also by Bio-Rad Laboratories are also useful solid matrixes. Use of a matrix comprised of an agarose derivative is discussed illustratively below.

The agarose matrix is typically activated for linking using cyanogen bromide. The activated matrix is then washed and linked to the desired antibody (receptor) molecules without drying of the activated matrix. The matrix-linked antibody is then washed and is ready for use. Unreacted reactive groups on the matrix can be reacted with an amine such as ethanolamine or Tris, if desired, although those reactive groups decay quickly. The affinity sorbant may be used in its loose state, as in a beaker or flask, or it may be confined in a column. Prior to use, it is preferable that the affinity sorbant be washed in the buffer or other aqueous medium utilized for purification of cell lysates containing the approximately 24,000 dalton polypeptide to eliminate non-specifically bound proteins or those antibodies that were unstably linked to the support.

An aqueous composition containing the SVHBV-3 vector-transfected cell lysate is provided, and is then admixed with the affinity sorbant. That admixture forms a reversible, linked antibody-antigen (receptor-ligand) complex between the linked antibody (receptor) and the approximately 24,000 dalton polypeptide (antigen).

The linked receptor-ligand complex is then separated from the remainder of the un-complexed aqueous composition to thereby obtain the polypeptide antigen in purified form linked to the affinity sorbant. When the admixture takes place in a beaker or flask, this separation can be made by filtration and washing. When the sorbant is in a column, the separation may take place by elution of the un-complexed aqueous medium, again, preferably, followed by a washing step.

When the purified polypeptide antigen is desired free from the affinity sorbant, it can typically be obtained by a variety of procedures. In any of those procedures, the reversible linked receptor-ligand complex is dissociated into its component parts of matrix-linked receptor and polypeptide antigen ligand, followed by separating that polypeptide antigen ligand from the linked-receptor to provide a solution of the purified polypeptide antigen ligand free from the affinity sorbant. The solution may be used as such, or it may be concentrated or dried prior to use as desired. In some instances, it may be desirable to desalt the solution prior to use, as is known.

The dissociation of the reversible complex may be effected in a number of ways. A 0.2 molar glycine hydrochloride solution at a pH value of about 2.5 is typically utilized. Alternatively, the bound polypeptide antigen ligand can be competed away from the linked receptor by admixture of the reversible complex with an excess of the immunogenic polypeptide utilized to raise the antibodies, e.g., polypeptide 99 where anti-99 antibodies are linked to the matrix. Such a competition avoids possible denaturation of the polypeptide antigen. Separation of the dissociated polypeptide antigen from the affinity sorbant may be obtained as above.

The preparation of affinity sorbants and their use is broadly old. However, such materials and uses that incorporate the antibody and antigen molecules of this invention have not been heretofore available. A detailed description of affinity sorbants, their methods of preparation and use wherein the antigen is linked to the matrix may be found in *Antibody as a Tool*, Marchalonis and Warr eds., John Wiley & Sons, New York, pages 64–67 and 76–96 (1982).

An exemplary ELISA utilizing the above method uses a solid support comprised of a before-described antigen of this invention adsorbed onto or otherwise affixed to a solid matrix comprised of the wells of a twelve or ninety-six well microtiter plate made of polystyrene or polyvinyl chloride to form the solid support. Non-specific binding sites on the microtiter well walls are thereafter typically blocked with a protein such as bovine serum albumin (BSA). Any unbound antigen and BSA are removed from the microtiter well as by rinsing.

A body sample aliquot such as human serum, blood or plasma is admixed with the above-described antigen-bound solid support to form an admixture containing solid and liquid phases. The solid-liquid phase admixture is maintained for a time period sufficient for anti-X protein antibodies in the body sample to immunoreact with the polypeptide antigen to form a polypeptide-containing immunoreaction product, e.g. about 30 minutes to about 2 hours. The solid and liquid phases are thereafter generally separated.

A liquid solution of a second, labeled, indicating means-containing, antibody, antibody combining site or S. aureus protein A that reacts with the first-named antibody is then admixed with the solid phase to form another solid-liquid phase admixture; i.e., a labeling reaction admixture. An exemplary second antibody is a peroxidase-labeled goat anti-human Ig antibody where the first-named antibodies are from a human body sample. Additional, useful enzyme labels include alkaline phosphatase, beta-D-galactosidase and glucose oxidase.

The admixture formed from the solid phase (the solid matrix-bound antigen-antibody immunoreaction product) and the second, labeled antibody solution is maintained (incubated) for a time period (e.g., about one hour) sufficient to form a reaction product between the bound first-named antibody and the indicating means such as a second immunoreaction between the two antibodies. The solid and liquid phases are thereafter separated.

The second antibody described above may also be specific for and immunoreact with only one of the classes of immunoglobulin (e.g., IgG, IgM, IgE, IgA, or IgD). Such antibodies provide the ability to identify the immunoglobulin class of anti-X protein antibody present in the body sample. In addition, the second antibody or antibody combining site may be specific for and immunoreact with only one of the two types of immunoglobulin light chains (e.g., kappa or lambda). These antibodies provide the ability to identify the isotype of the immunoglobulin molecule present in the body sample, and are well known.

A solution containing a substrate for the enzyme label such as hydrogen peroxide for peroxidase and a color-forming dye precursor such as o-phenylenediamine or 4-chloro-1-naphthol, or p-nitrophenyl phosphate for alkaline phosphatase, is thereafter admixed with the solid phase. The optical density at a preselected wavelength (e.g., 490 or 405 nanometers, respectively) may then be determined after a sufficient time period has elapsed (e.g., 60 minutes), and compared to the optical density of a control to determine whether anti-X protein antibodies were present in the body sample.

Another embodiment of this invention comprises a diagnostic system in kit form that includes a solid support comprised of a solid matrix such as a polystyrene twelve-well microtiter strip, and a before-described antigen of this invention absorbed (bound) or otherwise affixed to that solid matrix to form a solid support. This system preferably also includes separately packaged anti-human Ig antibodies having a linked indicating means such as peroxidase-labeled goat anti-human Ig antibodies, and may also include a substrate for the linked indicating means such as hydrogen peroxide and a color forming due precursor such as o-phenylenediamine, in separate packages. Hydrogen peroxide is typically not included in the kit due to its relative instability, and is typically supplied by the end user, although a container of hydrogen peroxide may also be a component of the diagnostic system. Buffer salts useful in an assay utilizing this system may also be included in one or more separate packages in dry or liquid form. A preferred polypeptide of this invention such as polypeptide 99 may also be included in a separate package for use in competitive binding studies as a control. An assay for the presence of anti-X protein antibodies in a body sample such as serum may be carried out with this diagnostic system using the before-described method.

6. Preparation of Polymers

The polypeptides of the present invention may be connected together to form a water-soluble or water-dispersible antigenic polymer comprising a plurality of the polypeptide repeating units. Such a polymer has the advantage of increased immunological reaction. Where different polypeptides are used to make up the polymer, such polymers have the additional ability to induce antibodies that immunoreact with a plurality of antigenic determinants of HBxAg.

A polymer may be prepared by synthesizing the polypeptides, as discussed hereinafter, to contain two cysteine residues. The two cysteine residues may be present at one terminus and within the polypeptide chain, or at both the amino- and carboxy-termini. A polypeptide containing two cysteines is referred to generally herein as a "diCys" polypeptide, while a polypeptide that contains two terminal cysteine residues is referred to herein as a "diCys-terminated" polypeptide. Such cysteine residues within the polypeptide chain or at the polypeptide chain termini may be present in the HBxAg sequence to which the polypeptide corresponds, e.g. the central cysteine of polypeptide 142 (the seventh residue from the carboxy-terminal alanine (Ala)), the carboxy-terminal cysteine (Cys) of polypeptide 99, or terminal cysteine residues may be added for the purpose of preparing the polymer.

Exemplary of useful diCys polypeptides are those represented by the formulae shown below, written from left to right and in the direction from amino-terminus to carboxy-terminus:

Polypeptide 8a: $R^1$-Gln-Leu-Asp-Pro-Ala-Arg-Asp-Val-Leu-Cys-Leu-Arg-Pro-Val-Gly-$R^2$;

Polypeptide 42a: Cys-Ser-Ala-Val-Pro-Thr-Asp-His-Gly-Ala-His-Leu-Ser-Leu-Arg-Gly-Leu-Pro-Val-Cys, Polypeptide 79a: Cys-Met-Glu-Thr-Thr-Val-Asn-Ala-His-Gln-Ile-Leu-Pro-Lys-Val-Leu-His-Lys-Arg-Thr-Leu-Gly-Cys, Polypeptide 99a: Cys-Leu-Ser-Ala-Met-Ser-Thr-Thr-Asp-Leu-Glu-Ala-Tyr-Phe-Lys-Asp-Cys, Polypeptide 100a: Cys-Leu-Phe-Lys-Asp-Trp-Glu-Glu-Leu-Gly-Glu-Glu-Ile-Arg-Leu-Lys-Val-Cys, and Polypeptide 142a: $R^1$-Ala-Pro-Ala-Pro-Cys-Asn-Phe-Phe-Thr-Ser-Ala-$R^2$, wherein $R^1$ and $R^2$ are each a cysteine residue, with the proviso that only one of $R^1$ and $R^{21}$ is present.

As is shown in FIG. 6, each of polypeptides 8, 42, 99, 100 and 142 contains a cysteine residue that is present in the amino acid residue sequence of the translated X-genome. It is reiterated that polypeptides having the amino acid residue sequences of polypeptides 99 and 100 except for the terminal cysteine residues are also useful herein in immunoreaction blocking studies and where coupling to a carrier by a means other than the MBS reaction, discussed hereinafter, is used.

When one or two terminal cysteine residues are added for the purpose of polymer preparation, and the remaining amino acid residue sequence corresponds to an antigenic determinant of HBxAg, the polypeptide repeating unit is still considered to correspond to an antigenic determinant of HBxAg.

In a typical laboratory preparation, 10 milligrams of the diCys polypeptide (containing cysteine residues in un-oxidized form) are dissolved in 250 milliliters of 0.1 molar ammonium bicarbonate buffer having a pH value of about 8. The dissolved diCys-terminated polypeptide is then air oxidized by stirring the resulting solution gently for a period of about 18 hours, or until there is no detectable free mercaptan by the Ellman test. (See Ellman (1959), *Arch. Biochem. Biophys.*, 82: 70–77.)

The polymer so prepared contains a plurality of the polypeptides of this invention as repeating units. Those polypeptide repeating units are bonded together by oxidized cysteine residues.

Such a polymer containing a plurality of the polypeptides of this invention can be represented by the formula, written from left to right and in the direction from amino-terminus to carboxy-terminus, $$(A)_a, (B)_b$$

wherein A and B are different polypeptide repeating units such as polypeptides 8, 42, 79, 99, 100 and 142. The subscript letters a and b are integers each having an average value of zero to about 2000 with the proviso that the sum of the average values for a and b is at least two, so that there are at least two polypeptide repeating units present in the polymer.

The sum of the average values of the superscript letters a and b are typically not greater than about 2000 so that the resulting polymer has an average molecular weight of about 5,000,000 daltons. In preferred practice, the average molecular weight of the polymer is about 50,000 to about 1,000,000 daltons.

The above formula is intended to be a generalized representation of the repeating units of the polymer and of the average number of each repeating units that is present. The polymers of this invention that contain two different repeating units are typically random copolymers. Thus, the formula shown hereinbefore is not intended to represent the order in which the polypeptides repeating units are present in the polymer, e.g. as in a block copolymer.

The above-described water-soluble or water-dispersible polymers of this invention are both immunogenic and antigenic, and are therefore described herein as antigenic, as discussed before. Such antigenic polymers when dispersed in a physiologically tolerable diluent and introduced as by immunizing injection in an amount of 400 micrograms of polymer per rabbit, are capable of inducing the production of antibodies in New Zealand Red rabbits that immunoreact with HBxAg. Exemplary physiologically tolerable diluents are well known in immunology and are discussed in further detail hereinafter.

7. Coupling of Polypeptides to Protein Carriers

The synthetic polypeptides utilized herein were coupled to keyhole limpet hemocyanin (KLH) using the following well known method. The KLH carrier was first activated with m-maleimidobenzoyl-N-hydroxysuccinimide ester, and was subsequently coupled to the polypeptide through a cysteine residue present at the polypeptide amino-terminus (polypeptide 100), the carboxy-terminus (polypeptide 99), or using the central cysteine of polypeptide 142, by a Michael addition reaction as described in Liu et al., *Biochem.* 80: 690 (1979).

A polypeptide of this invention may also be coupled to a carrier through different means, and may be coupled to carriers other than KLH. For example, a polypeptide, e.g. polypeptide 99b, may be coupled to a tetanus toxoid carrier through free amino groups, using a 0.04 percent glutaraldehyde solution as is well known. See, for example, Klipstein et al. (1983), *J. Infect. Disc.*, 147: 318.

Cysteine residues present at the amino- or carboxy-termini or in the central portion of the synthetic polypeptide have been found to be particularly useful for forming conjugates via disulfide bonds and Michael addition reaction products, but other methods well known in the art for preparing conjugates can also be used. Exemplary additional binding (linking) procedures include the use of dialdehydes such as glutaraldehyde (discussed above) and the like, or the use of carbodiimide technology as in the use of a water-soluble carbodiimide, e.g. 1-ethyl-3-(3-dimethylaminopropyl) carbodiimide, to form amide links between the carrier and polypeptide.

Useful carriers are well known in the art and are generally proteins themselves. Exemplary of such carriers are keyhole limpet hemocyanin (KLH), edestin, thyroglobulin, albumins such as bovine serum albumin or human serum albumin (BSA or HSA, respectively), red blood cells such as sheep erythrocytes (SRBC), tetanus toxoid, cholera toxoid as well as polyamino acids such as poly(D-lysine:D-glutamic acid), and the like.

As is also well known in the art, it is often beneficial to bind the synthetic polypeptide to its carrier by means of an intermediate, linking group. As noted before, glutaraldehyde is one such linking group. However, when cysteine is used the intermediate linking group is preferably an m-maleimidobenzoyl N-hydroxysuccinimide ester (MBS), also discussed before. MBS is typically first added to the carrier by an ester-amide interchange reaction. Thereafter, the above Michael reaction can be followed, or the MBS addition may be followed by a Michael addition of a blocked mercapto group such as thioacetic acid ($CH_3COSH$) across the maleimido-double bond. After cleavage of the acyl blocking group, and a disulfide bond is formed between the deblocked linking group mercaptan and the mercaptan of the added cysteine residue of the synthetic polypeptide.

The choice of carrier is more dependent upon the ultimate intended use of the antigen than upon the determinant portion of the antigen, and is based upon criteria not particularly involved in the present invention. For example, if an inoculum is to be used in animals, as for the production of anti-polypeptide antibodies to be used to assay for the presence of HBxAg, a carrier that does not generate an untoward reaction in the particular animal should be selected. If an inoculum such as a vaccine against HBxAg is to be used in man, then the overriding concerns involve the lack of immunochemical or other side reaction of the carrier and/or the resulting antigen, safety and efficacy-the same considerations that apply to any vaccine intended for human use.

8. Immunization Procedures

The inocula used for immunizations contain an effective amount of polypeptide, as a polymer of individual polypeptides linked together through oxidized cysteine residues or as a conjugate of the polypeptide linked to a carrier. The effective amount of polypeptide per inoculation depends, among other things, on the species of animal inoculated, the body weight of the animal and the chosen inoculation regimen as is well known. Inocula are typically prepared from the dried, solid polypeptide-conjugate or polypeptide polymer by suspending the polypeptide-conjugate or polypeptide polymer in water, saline or adjuvant.

These inocula typically contain polypeptide concentrations of about 20 micrograms to about 500 milligrams per inoculation. The stated amounts of polypeptide refer to the weight of polypeptide without the weight of a carrier, when a carrier was used.

The inocula also contain a physiologically tolerable (acceptable) diluent such as water, phosphate-buffered saline, or saline, and further typically include an adjuvant as part of the diluent. Adjuvants such as complete Freund's adjuvant (CFA), incomplete Freund's adjuvant (IFA) and alum are materials well known in the art, and are available commercially from several sources.

Inoculum stock solutions are prepared with CFA, IFA or alum as follows: An amount of the synthetic polypeptide-conjugate or polymeric polypeptide sufficient to provide the desired amount of polypeptide per inoculation is dissolved in phosphate-buffered saline (PBS) at a pH value of 7.2. Equal volumes of CFA, IFA or alum are then mixed with the polypeptide solution to provide an inoculum containing polypeptide, water and adjuvant in which the water-to-oil ratio is about 1:1. The mixture is thereafter homogenized to provide the inoculum stock solution.

Rabbits used herein to raise anti-polypeptide antibodies were injected subcutaneously with an inoculum comprising 200 micrograms of a polypeptide conjugate (polypeptide plus carrier) emulsified in complete Freund's adjuvant (CFA); 200 micrograms of polypeptide conjugate, incomplete in Freund's adjuvant (IFA); and 200 micrograms of polypeptide conjugate with 4 milligrams alum injected intraperitoneally on days 0, 14 and 21, respectively, of the immunization schedule. Each inoculation (immunization) consisted of four injections of the inoculum. Mice may be immunized in a similar way using about one tenth of the above dose per injection.

Animals are typically bled 4 and 15 weeks after the first injection. Control pre-immune serum was obtained from each animal by bleeding just before the initial immunization.

Control inoculum stock solutions can also be prepared with keyhole limpet hemocyanin (KLH), KLH in IFA (incomplete Freund's adjuvant), KLH-alum absorbed, KLH-alum absorbed-pertussis, edestin, thyroglobulin, tetanus toxoid, tetanus toxoid in IFA, cholera toxoid and cholera toxoid in IFA.

Upon injection or other introduction of the antigen or inoculum into the host animal, the immune system of the animal responds by producing large amounts of antibody to the antigen. Since the specific antigenic determinant of the manufactured antigen; i.e., the antigen formed from the synthetic polypeptide linked to the carrier or the polymer, corresponds to the determinant of the natural antigen of interest, the host animal manufactures antibodies not only to the synthetic polypeptide antigen, but also to the protein or polypeptide to which the synthetic polypeptide antigen corresponds; i.e., to HBxAg.

9. Deposits

The materials enumerated below were placed on deposit in the American Type Culture Collection on Mar. 8, 1984 and have the accession numbers indicated for each. All designations for cell lines, vectors and the like that include the letters "ATCC" followed by numbers and/or letters and numbers refer to materials deposited with the above American Type Culture Collection, 12301 Parklawn Drive, Rockville, Md. 20852.

| Material | ATCC Accession Number |
| --- | --- |
| mixture of virus SVHBV-3 and SV40 $tsA_{239}$ helper virus. | VR 2084 |
| Vector DNA | |
| SVHBV-3 | 40102 |
| AM6 | 40101 |
| SVAM191 | 40103 |
| E. coli | |
| EC-AM6 | 39630 |
| EC-AM1 | 39629 |
| EC-SVAM191 | 39631 |

In addition to the above materials deposited with the ATCC by the present inventors, materials prepared by others and used herein have also been deposited with the ATCC. A list of those materials is provided below:

| Material | ATCC Accession Number |
| --- | --- |
| E. coli | |
| W3110 | 27325 |
| 294 | 31446 |
| RR1 | 31447 |
| HB101 | 33694 |
| Mammalian Cells | |
| HepG2 | CCL 23 |
| BSC-1 | CCL 26 |

| Material | ATCC Accession Number |
| --- | --- |
| COS-7 | CRL 1651 |
| PLC/PRF/5 Vector | CRL 8024 |
| pBR322 | 37017 |

B. Materials and Methods

1. HBV DNA Isolation and Preparation

Region XHBV DNA was isolated from Dane particles, subtype adw, from the plasma of an HBsAg-positive human donor (National Institutes of Health #737139) following the procedure of Robinson (*Am. J. Med. Sci.*, (1975) 270: 151–159). Briefly, 1.0 ml of plasma was diluted to 3.0 ml with TN buffer which contained 0.001 molar (M) Tris-HCl (pH 7.4) and 0.5 M HCl. The diluted plasma was centrifuged at 10,000 xg for ten minutes to remove large debris, and then layered over 2.5 milliliters (ml) of 30 percent (W/V) sucrose containing TN, 0.001 M-EDTA (0.1 percent 2-mercaptoethanol and 1 milligram/milliliter (mg/ml) bovine serum albumin (BSA) that had been previously centrifuged at 10,000 xg for 10 minutes to remove precipitated BSA). After centrifuging for 4 hours at 50,000 rpm, 4° C. in a Spinco SW-65 rotor (Beckman Instruments, Inc.), the supernatant was carefully removed and the pellet was resuspended in 50 microliters of TN buffer containing 1 percent Nonidet P-40 (polyoxyethylene (9) octyl phenyl ether; Sigma Chemical Co., St. Louis, Mo.) and 0.1 percent 2-mercaptoethanol.

The single stranded portion of the HBV DNA isolated above was made double-stranded by adding 25 microliters of mix E (0.2M Tris-HCl (pH 7.4), 0.08 M $MgCl_2$, 0.24 $NH_4Cl$, 1.0 millimolar (mM) each of dATP, dTTP, dGTP, and dCTP) to the 50 microliters of resuspended HBV DNA, followed by incubating at 37° C. for 3 hours. Robinson (1975), *Am. J. Med. Sci.*, 270: 151–159.

Radioactively labeled HBV DNA to be used as a genomic probe was made using the above filling-in procedure by substituting 0.25 microliters each of 3HdCTP and 3HdGTP (both 21 curies per mM) for dCTP and dGTP respectively.

2. HBxAg Cloning

A portion of the HBV genome containing the DNA sequence coding for HBxAg was cloned using the plasmid pBR322 introduced into *E. coli*. Double-stranded, unlabeled HBV DNA isolated above was digested with the restriction endonuclease Bam HI (50 mM NaCl, 10 mM Tris-HCl (pH 7.5), 10 mM MgCl, 1 mM dithiothreitol). The reaction mixture was electrophoresed in a 0.6% agarose horizontal slab gel at 100 amperes for 2 hours (0.04 Tris-Acetate, 0.002M EDTA).

Staining with 1 percent ethidium bromide revealed three HBV DNA fragments, indicating the presence of two Bam HI restriction sites in the genome. A 3200 base pair (bp) fragment represented the entire HBV genome in linear form as a result of being cut at only one of the Bam HI sites. The 1850 bp and 1350 bp fragments represented the genome cut into two fragments as a result of complete Bam HI digestion.

Copies of the three Bam HI HBV DNA restriction fragments isolated above were obtained by cloning in the plasmid pBR322 (ATCC 37017) (Sutcliffe (1978), *P. Natl. Acad. Sci., USA*, 75: 3737–3791). To insert the HBV DNA Bam HI fragments into pBR322, the plasmid was linearized by digesting with Bam Hi (50 mM NaCl, 10 mM Tris-HCl (pH 7.5), 10 mM $MgCl_2$, 1 mM dithiothreitol) to form termini complimentary to those of the HBV fragments. The three HBV DNA fragments and the pBR322 fragment were mixed, and were subjected to DNA ligation with T4 DNA ligase (66 mM Tris-HCl (pH 7.6), 66 mM $MgCl_2$, 10 mM dithiothreitol and 0.4 mM ATP). The ligation reaction product obtained in the above reaction is a circular DNA derived from the linearized pBR322 and HBV fragments joining at their complimentary termini.

The circular recombinant plasmids were introduced into *E. coli* strain HB101 (ATCC 33694; provided by Dr. Dean Hunter of the National Cancer Institute, NIH, Bethesda, Md.) following the procedure of Cohen et al. (1972), *Proc. Natl. Acad. Sci. USA*, 69: 2110–2114. Briefly, an *E. coli* HB101 culture was incubated in a solution of 0.03M $CaCl_2$ at 0° C. for 20 minutes. About $5 \times 10^9$ bacterial cells were added to 0.3 ml of the same solution to which was added 100 nanograms (ng) of recombinant plasmids. This transformation reaction mixture was incubated at 0° C. for 60 minutes.

The plasmid pBR322 contains ampicillin and tetracycline resistance-conferring genes. Drug sensitive bacterial cells transformed with this plasmid exhibit ampicillin and tetracycline resistance. Since the pBR322 DNA has only one Bam HI cleavage site that is on the tetracycline resistance gene, insertion of the HBV fragments at the Bam HI site disrupts this gene. Drug sensitive *E. coli* HB101 transformed with a plasmid derived from pBR322 with a HBV DNA fragment inserted at the Bam HI site (cloning vector) therefore exhibit ampicillin resistance and tetracycline sensitivity.

Transformed *E. coli;* i.e., those containing the plasmid ampicillin resistance conferring gene, were selected by plating the transformation reaction mixture onto an LB broth agar medium (a growth medium containing, per liter thereof, 10 g Bactoagar, 10 g Bactotryptone, 5 g Bacto yeast extract (each from Difco Labs, Detroit, Mich.) and 5 g NaCl) containing 50 micrograms per ml of ampicillin. The plated *E. coli* were incubated at 37° C. for 2 days.

From among the colonies that exhibited ampicillin resistance after transformation by the above procedure, tetracycline-sensitive colonies were selected by plating the colonies onto an LB broth, above, containing 50 micrograms per ml of tetracycline, instead of ampicillin. Those plated colonies were also incubated at 37° C. for 2 days. *E. coli* HB101 strains containing pB322 with HBV DNA fragments inserted at the Bam HI cleavage site in the tetracycline resistance gene were thus obtained.

3. Plasmid DNA Extraction

The *E. coli* HB101 cells containing the recombinant DNA as isolated above were grown in the LB broth medium containing 20 micrograms/ml ampicillin, with the addition of chloramphenicol to the concentration of 170 micrograms/ml in the logarithmic growth phase. The cultivation was continued for several hours for amplifying the plasmid DNA.

The cells were then lysed by admixing 5 ml of a 25 percent sucrose in 50 mM Tris-HCl (pH 8.0) solution to 500 ml of cells. After incubation for 10 minutes at 0° C., 1 ml of a 1 percent lysozyme in 0.25M Tris-HCl (pH 7.5) solution was admixed. After incubation for 10 minutes at 0° C., 2 ml of 0.25M EDTA (pH 8.0) was gently admixed. After incubation for 10 minutes at 0° C. 8 ml of 1 percent Triton X-100

(polyoxyethylene (9) octyl phenyl ether) in 0.15M Tris-HCl (pH 8.0), 0.2M EDTA (pH 8.0) was admixed and again incubated for 10 minutes at 0° C.

The resulting lysate was centrifuged at 30,000 rpm in a Spinco SW-65 rotor (Beckman Instruments) to remove denatured protein and cell debris. DNA was precipitated from the cleared lysate by admixing 1/10 volume of 2.5 sodium acetate and 2.5 volumes of 99 percent ethanol, and incubating at −20° C. for 30 minutes. The DNA precipitate was pelleted by centrifugation at 10,000 xg for 30 minutes.

Deproteinization was performed twice with 1 ml of phenol saturated with 0.01M Tris-HCl (pH 7.6), 0.1 M NaCl and 0.0012M EDTA. Landers et al. (1977), *J. Virol.* 23: 368–376. The aqueous layer from the above procedure was taken, and the DNA precipitated therefrom by adding 1/10 volume 2M sodium acetate and 2.5 volumes of 99 percent ethanol and incubating at −20° C. for 20 minutes. Centrifugation for 10 minutes at 10,000 xg yielded a pellet of completely double stranded DNA including the gene coding for HBxAg.

4. Plasmid DNA Analysis

The presence of HBV DNA in the clones was confirmed using the Southern transfer and hybridization technique. Southern (1975), *Mol. Biol.*, 98: 503. 10 Mg of plasmid DNA from each clone isolated as above was digested with the Bam HI (50 mM NaCl, 10 mM Tris-HCl (pH 7.5), 10 mM MgCl$_2$, 1 mM dithiothreitol). The reaction mixture was electrophoresed in an 0.6 percent agarose horizontal slab gel at 100 amperes for 2 hours (0.04M Tris-acetate, 0.002M EDTA).

The DNA in the gel was denatured by soaking the gel in several volumes of 1.5M NaCl and 0.5M NaOH for 1 hour at room temperature with constant stirring or shaking. In some instances, the DNA in the gel was hydrolyzed by acid depurination prior to alkali denaturation by soaking the gel twice for 15 minutes in 0.25M HCl at room temperature. After denaturation, the gel was neutralized by soaking in several volumes of a solution of 1M Tris-HCl (pH 8.0) and 1.5M NaCl for 1 hour at room temperature with constant shaking.

The DNA in the gel was transferred onto nitrocellulose essentially as described in Maniatis et al. (1982), *J. Molecular Cloning*, Cold Spring Harbor. Briefly, nitrocellulose (Catalogue No. BA85, Schleicher & Schuel, Ohio) was placed on top of the gel and several layers of Whatman 3MM paper are placed over the nitrocellulose. This sandwich was then placed gel side down on a Whatman 3MM wick whose ends were immersed in a buffer containing 0.9M NaCl and 0.09M sodium citrate. The capillary movement of the buffer thereby transferred the DNA from the gel to the nitrocellulose. The DNA was fixed to the nitrocellulose by baking at 80° C. for 2 hours under vacuum. The plasmid DNA on the nitrocellulose prepared above (Southern filters) was probed for the presence of HBV DNA fragments using the procedure of Maniatis et al., supra.

Briefly, the Southern filters were prehybridized by soaking in prehybridization fluid 0.9M NaCl, 0.09M sodium citrate, 0.5 percent SDS (sodium dodecyl sulfate), 100 mg/ml denatured salmon sperm DNA and 5X Denhardt's Solution (containing, per liter thereof, 1 g Ficoll, 1 g polyvinylpyrrolidone, and 1 g BSA Fraction V) for 4 hours at 68° C.

Hybridization was performed in a heat-sealable plastic bag with just enough hybridization solution to keep the Southern filter wet (50 microliters/cm$^2$ of filter). Hybridization solution contained 0.9M NaCl, 0.09M sodium citrate, 0.01M EDTA, 5X Denhardt's solution, 0.5 percent SDS, 100 micrograms/ml denatured salmon sperm DNA and 5×10$^7$ cmp of the radioactively labeled HBV DNA prepared above. The Southern filter was incubated in the hybridization solution for 12 hours at 68° C.

After washing the filter for 2 hours (0.3M NaCl, 0.03M sodium citrate), x-ray film (XRP-1, Kodak) was exposed to the filter to obtain an autoradiographic image.

Three recombinant plasmids were isolated using the above procedure and designated AM6, AM7 and AM1. AM6 contained pBR322 DNA and the entire HBV genome. AM7 contained pBR222 DNA and a 1350 bp HBV DNA fragment. AM1 contained pBR322 DNA and an 1850 bp HBV DNA fragment including the gene coding for HBxAg.

Figure 4:
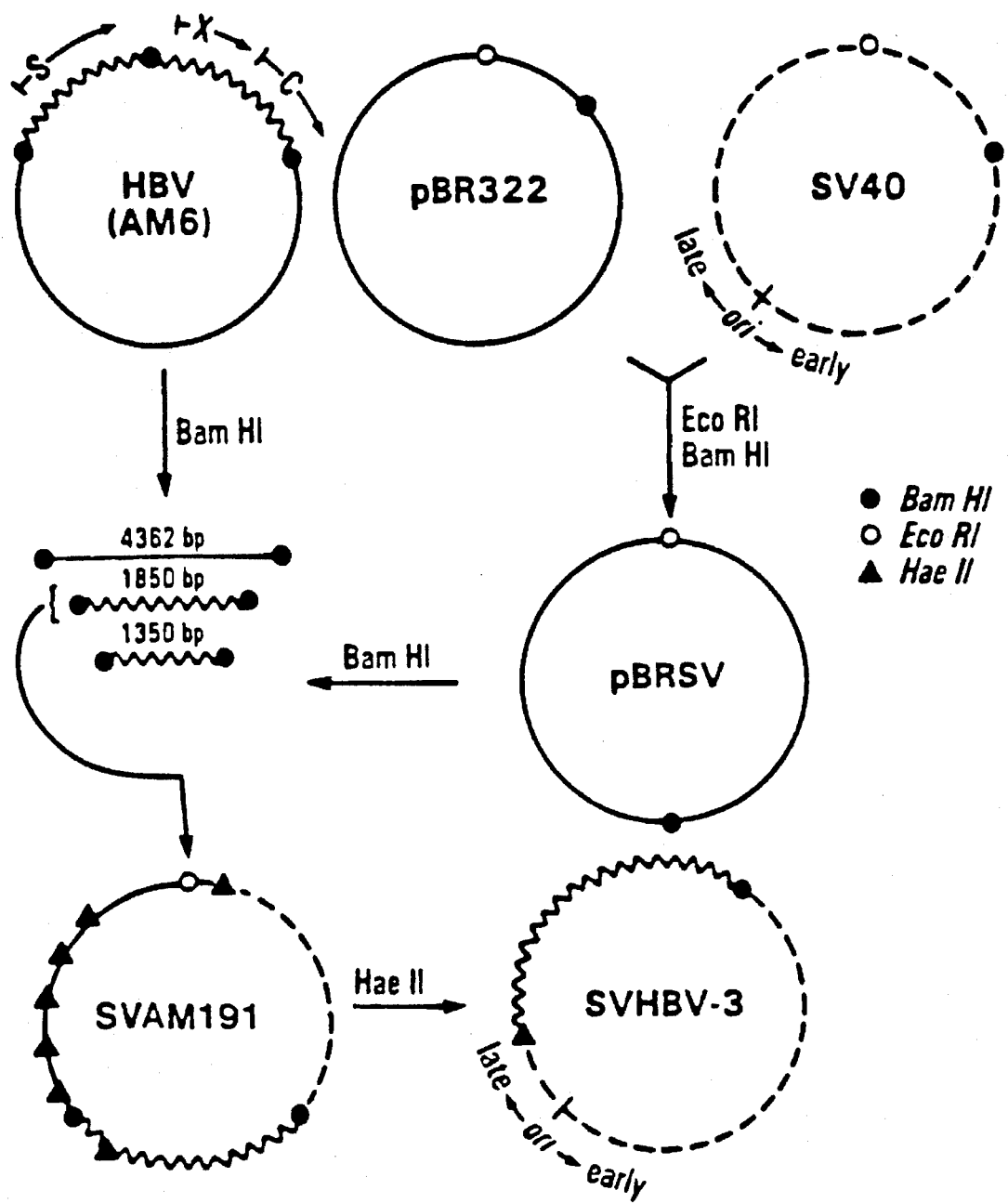
FIG. 4 schematically illustrates the method, described in the Materials and Methods section hereinafter, used for inserting DNA fragments into vectors of this invention made from AM6 (wavy lines), pBR322 (solid lines) and SV40 (dashed lines) to produce the cloning vector SVAM191 and then the expression vector SVHBV-3 that expresses a substantial portion of HBxAg. Relative positions of restriction endonuclease sites for Bam HI, Eco RI and Hae II are illustrated by closed circles, open circles and closed triangles, respectively. The origin (ori) and early and late promoters of the SV40 genome are also indicated.

5. Construction of a Replication Plasmid Containing an SV40/HBxAg Expression Vector DNA Defective SV40 virus obtained from Dean Hamer, supra, was subjected to Bam HI and Eco RI cleavage in a buffer containing 50 mM NaCl, 10 mM Tris-HCl (pH 7.5), 10 mM MgCl$_2$, and 1 mM dithiothreitol. Plasmid pBR322 DNA was subjected to the double digestion discussed before so as to form termini complementary to the SV40 DNA so cleaved. The cleavage products of each of these digestions were separated and purified by cesium chloride density gradient centrifugation. Tanaka et al. (1975), *J. Bact.*, 121: 354–362. The 4492 bp SV40 fragment and 3987 bp pBR322 fragment so isolated were subjected to DNA ligation with T4 DNA ligase in a buffer containing 66 mM Tris-HCl (pH 7.6), 6.6 mM MgCl$_2$, 10 mM dithiothreitol, and 0.4 mM ATP to form pBRSV (FIG. 4).

The ligation reaction product obtained in the above reaction is a circular DNA derived from the linearized pBR322 3987 bp and SV40 4492 bp fragments joining at their complementary Eco RI and Bam HI termini. This circular plasmid was then linearized by cleavage at the Bam HI restriction site formed during ligation creating Bam HI cohesive termini at each end.

An 1850 bp HBV DNA fragment including the gene coding from HBxAg was isolated by subjecting plasmid AM6 isolated above to digestion with Bam HI in a buffer containing 50 mM NaCl, 10 mM Tris-HCl (pH 7.5), 10 mM MgCl$_2$, and 1 mM dithiothreitol. The reaction mixture was subjected to electrophoresis at 100 amperes for 2 hours using 0.8 percent agarose and the 1850 bp band was cut out and melted at 68° C. for 15 minutes. 1/10 Volume of 3M sodium acetate was added, and the resulting solution was subjected to the deproteinization procedure described before.

The HBxAg gene-containing HBV DNA fragment thus isolated had Bam HI complementary termini. This DNA fragment was then ligated to the pBR-SV prepared above using T4 DNA ligase in a buffer containing 66 mM Tris-HCl (pH 7.6), mM MgCl$_2$, 10 mM dithiothreitol, and 0.4 mM ATP.

The product of the above ligation reaction was a circular plasmid DNA designated SVAM191. It contained, in clockwise order, a 4492 bp SV40 DNA fragment from its Bam HI site at base position 2468 to its Eco RI site at base position 1717, a 3987 bp pBR222 DNA fragment from its Eco RI site at base position 0 to the Bam HI site at base position 375 and an 1850 bp HBV DNA fragment from its Bam HI site at base position at 1400 to the Ram HI site at base position 28 plasmid SVAM191 is shown schematically in FIG. 4.

SVAM191 was introduced into *E. coli* HB101 using the transformation procedure described above. Since these transformed *E. coli* were also ampicillin resistant and tetracycline sensitive, they were subjected to the same isolation procedure described before for the *E. coli* cloning vector. The procedures for production, isolation, purification and analysis described before were employed to obtain milligram quantities of substantially pure SVAM191 DNA.

6. Construction of SV40/HBxAg Expression Vector

A vector capable of inducing the production of HBxAg in eucaryotic cells was made by excising a portion of SVAM191 DNA. This was accomplished by digesting SVAM191 DNA with Hae II endonuclease in a buffer containing 10 mM Tris-HCl (pH 7.5), 10 mM $MgCl_2$, and 1 mM dithiothreitol to cleave SVAM191 at the Hae II sites at base position 767 in the SV40 DNA region and base position 1437 in the HBV DNA region.

The two DNA fragments obtained from the above reaction were separated by the electrophoretic agarose gel procedure described before. The larger fragment so isolated containing only SV40 and HBV DNA was circularized by subjecting its Hae II complementary termini to the T4 DNA ligation procedure described before.

Figure 5:
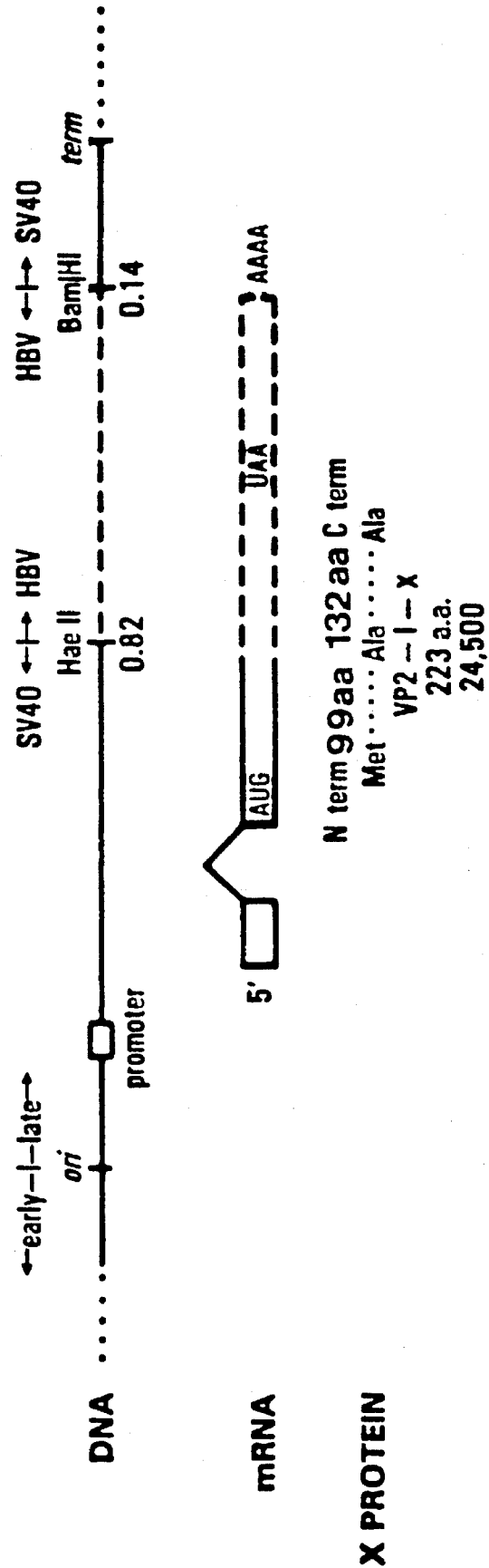
FIG. 5 depicts a linear portion of the SVHBV-3 recombinant expression vector containing the genes for the SV40 late promoter, the amino-terminal 99 amino acid residues (99aa), and a substantial polypeptide portion (132aa; 132 of 154 amino acid residues) of the HBxAg gene sequence coding for the 132 carboxy-terminal amino acid residues. Also depicted is the mRNA for the VP2 HBxAg fusion protein expressed by the vector.

The circular DNA expression vector formed above was designated SVHBV-3 (FIGS. 4 and 5). It contains expression control elements from SV40 and a gene coding for HBxAg from HBV.

7. Transfection of Eucaryotic Host Cells with SVHBV-3

The BSC-1 African Green Monkey kidney cell line (ATCC CCL 26; obtained from Dr. G. B. Thornton, Johnson & Johnson Biotechnology Center, Inc., La Jolla, Calif.), a permissive host for SV40, was chosen for transfection with SVHBV-3. Confluent monolayers of about $10^7$ cells were obtained by culturing at 37° C. in Eagle's minimal essential medium (EMEM) supplemented with 10 percent fetal calf serum, 100 units of penicillin/ml, 100 micrograms/ml streptomycin and 3 mM L-glutamine. The monolayers were infected with vector SVHBV-3 DNA in the presence of DEAE-dextran as described by Ganem et al. (1976), *J. Mol. Biol.*, 101: 57–83.

One flask was infected with 1.6 micrograms of the recombinant SVHBV-3 together with 0.05 micrograms of SV40 $tsA_{239}$ DNA as helper. Controls received equivalent amounts of the vector helper DNAs alone. The cultures were incubated at 40° C. for 12 days, and were then lysed by freeze-thawing, and stored at −70° C.

Cellular proteins were extracted from the freeze-thawed cell powders obtained above by first adding 2 mg of cell powder to 1 ml of protein extraction buffer (2 percent SDS, 10 percent glycerol, 0.08M Tris-HCl (pH 6.8), 2 mM phenyl methyl sulfonyl fluoride, 0.1M dithiothreitol, 0.001 percent bromphenol blue). The solution was then boiled for 5 minutes, centrifuged at 15,000 rpm for 10 minutes and the supernatants collected therefrom.

An amount of supernatant sufficient to provide 100 micrograms of sample protein was then subjected to SDS-polyacrylamide gel electrophoresis in the Western Blot procedure described below.

8. Polypeptide Syntheses

The polypeptides of this invention were chemically synthesized by solid-phase methods as described in Merrifield et al. (1963), *J. Am. Chem. Soc.* 85: 2149; Merrifield et al. (1970), *A. Rev. Biochem.* 39: 841–866 and Houghten et al. (1980), *Int. J. Peptide Prot. Res.* 16: 311–320. The relatively short polypeptides used herein correspond to antigenic determinants of HBxAg.

FIG. 6 shows the 154 amino acid residue sequence of HBxAg. The amino acid residue sequences of the preferred synthetic polypeptides described herein (99, 100 and 142) are also shown in FIG. 6. The composition of both synthetic polypeptides was confirmed by amino acid analysis.

Generally, an immunogen or synthetic polypeptide is made by the steps of providing a plurality of suitably protected amino acids that correspond to the amino acid residues of an antigenic determinant domain of HBxAg, and synthesizing those amino acids into a polypeptide that has an amino acid residue sequence corresponding to the polypeptide amino acid residue sequence of that antigenic determinant. The produced synthetic polypeptide can be used to produce an inoculum, usually by linking it to a carrier to form a conjugate and then dispersing an effective amount of the conjugate in a physiologically tolerable diluent.

The polypeptides are preferably synthesized according to the above-referenced solid phase methods using a cysteine resin. See Merrifield et al., *J. Am. Chem. Soc.*, supra. Using that method, the alpha-amino group of each added amino acid is typically protected by a tertiary-butoxycarbonyl (t-BOC) group prior to the amino acid being added into the growing polypeptide chain. The t-BOC group is then removed prior to addition of the next amino acid to the growing polypeptide chain. The side chains on individual amino acids are protected as follows: Arg-tosyl; Ser-, Thr-, Glu- and Asp- O-benzyl; Tyr-O-bromobenzyloxy carbamyl; Trp-N-formyl; S-methoxybenzyl for cysteine; 2-chlorobenzoxycarbonyl for lysine; and dinitrophenyl for histidine. When asparagine is used, an equal molar amount of N-hydroxy-benztriazole is added with the protected amino acid and dimethyl formamide (DMF) is used as the coupling solvent. The N-formyl group on the Trp residues is removed after cleavage of the polypeptide from the resin support by treatment with 1.0 molar ammonium bicarbonate at a polypeptide concentration of 1.0 milligram/milliliter for 16 hours at the room temperature. Yamashiro et al. (1973), *J. Org. Chem.* 38: 2594–2597. The efficiency of coupling at each step can be monitored with ninhydrin or picric acid, and is preferably greater than 99 percent in all cases. See Gisin (1972), *Anal. Chem. Acta* 58: 248–249; and Kaiser (1980), *Anal. Biochem.* 34: 595–598.

After preparation of a desired polypeptide, a portion of the resulting, protected polypeptide (about 1 gram) is treated with two milliliters of anisole, and anhydrous hydrogen fluoride, about 20 milliliters, is condensed into the reaction vessel at dry ice temperature. The resulting mixture is stirred at about 4° C. for about one hour to cleave the protecting groups and to remove the polypeptide from the resin. After evaporating the hydrogen fluoride at a temperature of 4° C. with a stream of $N_2$, the residue is extracted with anhydrous diethyl ether three times to remove the anisole, and the residue is dried in vacuo.

The vacuum dried material is extracted with 5% aqueous acetic acid (3 times 50 milliliters) to separate the free polypeptide from the resin. The extract-containing solution is lyophilized to provide a monomeric unoxidized polypeptide.

Briefly, as a generalized procedure for each polypeptide, 4 milligrams of KLH in 0.25 milliliters of 10 millimolar sodium phosphate buffer (pH 7.2) is reacted with 0.7 milligrams of MBS dissolved in DMF, and the resulting admixture is stirred for 30 minutes at room temperature. The MBS solution is added dropwise to ensure that the local concentration of DMF was not too high, as KLH is insoluble at DMF concentrations of about 30% or higher. The reaction product, KLH-MB, is passed through a chromatography column prepared with Sephadex G-25 (Pharmacia Fine Chemicals, Piscataway, N.J.) equilibrated with 50 millimolar sodium phosphate buffer (pH 6.0) to remove free MBS. KLH recovery from peak fractions of the column eluate, monitored at 280 nanometers, is typically approximately 80%.

The KLH-MB so prepared is then reacted with 5 milligrams of polypeptide dissolved in 1 milliliter of buffer. The pH value of the resulting reaction composition is adjusted to 7–7.5, and the reaction composition is stirred at room temperature for 3 hours to provide a polypeptide-carrier conjugate.

9. Western Blotting

The anti-polypeptide antibodies (anti-99, anti- 100 and anti-142) were examined using the Western Blot technique to confirm their predicted specificity for HBxAg, and to confirm the expression of the substantial polypeptide portion of HBxAg in transfected cells. The cellular proteins including HBxAg were separated by 12.5 percent SDS-polyacrylamide gel electrophoresis. See Laemmli (1970), *Nature*, 277: 680–685; and Towbin et al. (1979), *Proc. Natl. Acad. Sci., USA*, 76: 4350–4354.

Proteins were electrophoretically transferred to nitrocellulose (Schleicher & Schuel, Catalogue No. BA85) as described by Towbin et al., supra, using an electroblot apparatus (E.C. Apparatus Corp. of Jacksonville, Fla.) with a buffer consisting of 25 mM Tris-Base, 192 mM glycine, 20 percent methanol and 0.1 percent SDS (pH 8.3). Following the transfer, the nitrocellulose was blocked in BLOTTO (Bovine Lacto Transfer Technique Optimizer, Johnson et al. (1983), *J. Exp. Med.*, 159: 1751–1756; 5% (w/v) non-fat dry milk; 0.01% anti-foam A (Sigma, Catalogue No. A5758), and 0.0001% merthiolate (Sigma, Catalogue No. 5125) in PBS at pH 7.2) to reduce non-specific binding. The blots were reacted with 100 microliters of antipeptide antibody in 10 ml of BLOTTO for 3 hours and then washed 3 times for 1 hour with 50 ml of fresh BLOTTO.

Anti-polypeptide antibodies bound to vector-specific protein were detected by reacting the blots with 20 microliters of $^{125}$I-labeled *Staphylococcus aureus* protein A in 10 milliliters of BLOTTO for 1 hour. The blots were then washed in 50 milliliters of fresh BLOTTO for 15 minutes 4 times and then under a continuous flow of water for 20 minutes.

10. $^{125}$I Labeling of Hepatoma Cell Extracts

Monolayers of the human hepatoma-derived cell line PLC/PRF/5 known to contain integrated sequences of HBV (Alexander et al. (1976), *African Med. J.*, 50: 21–24; ATCC CRL 8024) were lyophilized. The cell powder was dissolved in phosphate-buffered saline (PBS) to achieve a 1 mg/ml protein concentration. After centrifugation at 10,000 xg to remove cellular debris, 50 microliters of the above solution were admixed with 75 microliters of RIPA (0.15M NaCl, 10 mM sodium phosphate (pH 7.5), 1% Nonidet P-40, 0.5% sodium deoxycholate, 0.1% SDS) and 20 microliters of 0.2M sodium phosphate (pH 7.5). In one study, the thus solubilized cell protein was labeled with 5 milliCuries (mCi) of $^{125}$I using the chloramine T reaction. In the study shown in FIG. 7, the cell lysates were labeled with 3 microCuries (μCi) of $^{125}$I using the same reaction. The above reaction mixture was run through the Sephadex G-25 (Pharmacia Fine Chemicals, Piscataway, N.J.) column washed with PBS. The radiolabeled peak fraction ($9 \times 10^6$ cpm/ml) obtained was pre-incubated with normal rabbit serum to remove nonspecific binding. Briefly, 20 microliters of a peak fraction were admixed with 1.0 ml of RIPA, 20 microliters Trasylol (a trademark for aprotinin, Sigma, February, 1984 Catalogue, page 163) and 100 microliters of NRS. After incubation for 1 hour at 0° C. 500 microliters of formalin-fixed *S. aureus* (Staph A; Calbiochem, La Jolla, Calif.) cells were admixed, and the admixture was incubated at 0° C. for 30 minutes. The Staph A precipitate was removed by centrifugation at 10,000 xg for 10 minutes, and the supernatant was recovered.

11. Immunoprecipitations (IP)

Rabbit anti-polypeptide antiserum against polypeptide 99 (anti-99) was reacted with the above obtained radioiodine-labeled cell proteins. Briefly, 10 microliters of anti-99 was admixed with $2 \times 10^6$ cpm of labeled extract and incubated for 1 hour at 0° C. 40 Microliters of Staph A were then admixed and incubated for 30 minutes at 0° C. The Staph A precipitate was removed by centrifugation at 10,000 xg for 10 minutes, and the pellet was recovered. The pellet was resuspended in 1 ml of RIPA and centrifuged as above. The resulting pellet was resuspended in 1.0 ml LiCl solution (100 mM Tris HCl, 500 mM LiCl), and was again centrifuged. The LiCl solution treatment was repeated and the pellet recovered.

The above-obtained pellet was resuspended in 50 microliters of sample buffer and boiled for 3 minutes. The mixture was centrifuged at 10,000 xg for 1 minute and the supernatant recovered, and was subjected to 12.5 percent SDS-polyacrylamide gel electrophoresis. The above gels were exposed to XRP-1 x-ray film to obtain an autoradiograph.

12. Preparation and Assay of Chimpanzee And Human Liver Cell Extracts

Liver samples from two HBV chronically infected chimpanzees and a human, and from normal chimpanzee and human (HBV sero-negative) livers were quick frozen in liquid nitrogen, and were ground to a powder. The powders were admixed into sample buffer (0.0625M Tris-HCl (pH 6.8), 2% SDS, 10% glycerol, 5% 2-mercaptoethanol and 0.001% bromophenol blue) and boiled for 5 minutes. The mixture was centrifuged at 10,000 xg for 30 minutes to remove cell debris. The samples were then subjected to Western Blot analysis as described before using 75 micrograms of protein per gel lane.

13. Identification of Anti-HBxAg Antibodies in Human Sera

20 Micrograms per lane of SVHBV-3 transfected BSC-1 cell extracts were subjected to SDS-PAGE on 12 percent acrylamide gels, and the separated proteins were transferred electrophoretically to nitrocellulose sheets as before-described. The resulting nitrocellulose sheets were admixed with 1:50 dilutions of serum from six humans that had been diagnosed as having HBV-related infections, including a symptomatic carrier and a patient with a hepatocellular carcinoma. Control sheets were admixed with rabbit-anti-polypeptide antibodies of this invention.

The nitrocellulose-protein serum admixtures were maintained for 2 hours at room temperature. The sheets were then rinsed and admixed with a 1:200 dilution of goat anti-human or anti-rabbit antibodies linked to horseradish peroxidase, as was appropriate. That admixture was maintained for a time period of 1 hour for bound anti-X antibodies to react with the appropriate anti-antibodies. The sheets were washed and then developed with 4-chloro-1-naphthol, as previously described. The serum from the patient with hepatocellular carcinoma exhibited strong immunoreactivity with the approximately 24,000 dalton polypeptide expressed by the SVHBV-3 transfected cells.

14. Cell Lines and Tissue Samples

PLC/PRF/5 and HepG2 cells were provided by Drs. D. Milich Department of Basic & Clinical Research, Scripps Clinic and Research Foundation (Scripps), La Jolla Calif. Chimpanzee liver tissue samples were provided by Drs. R. Purcell and P. Kaplan of the National Institute of Allergy and Infectious Diseases, Bethesda, Md., and Ortho Diagnostics, Inc., Raritan, N.J., respectively. Human liver tissue samples were provided by Drs. F. Chisari, J. Dienstag and A. Yu of Scripps, Department of Medicine, Harvard University, Boston, Mass., and Department of Pediatrics, University of California-San Diego, La Jolla Calif., respectively.

EXAMPLES

1. Preparation and Use of Diagnostic Systems for Detecting Anti-HBxAg Antibodies (HBxAb)

Polypeptides 8, 42, 79, 99, 100, and 142 ( also referred to herein as p8, p42, p79, p99, p100 and p142) were synthesized by symmetrical anhydride chemistry on a Model 430A Applied Biosystems (Foster City, Calif.) solid phase peptide synthesizer according to the method of Hagenmeier et al., *Hoppe-Sevler's Z. Physiol. Chem.*, 353: 1973–1976 (1972).

Each polypeptide was solubilized in deionized water (pH 6) at a concentration of 1 milligram per milliliter (mg/ml). One hundred microliters (μl) of 10 millimolar (mM) sodium borate buffer, pH 9, containing 1 microgram (μg) of polypeptides p8, p42, p79, p99, p100 or p142 were admixed into the wells of 96-well EIA microtiter plates (Costar, Van Nuys, Calif.). The plates were then maintained for about 16 hours at 37° C. to permit the buffer to evaporate and the polypeptides to adsorb onto (affix to) the walls of the wells. Three hundred μl of T-wash (Tris-buffered saline: 50 mM Tris base, 150 mM NaCl, pH 7.6) containing 10% normal horse serum, 5% normal goat serum, 5% fetal calf serum and 0.05% Tween-20 were then admixed into each well to block excess protein binding sites.

The wells were maintained 2 hours at 37° C., the blocking solution was removed by shaking, and the wells were dried by maintaining them for 1 hour at 37° C., thus forming a diagnostic system of the present invention; i.e., a HBxAg-related polypeptide-containing solid support (polypeptide-coated well).

The polypeptide-containing solid supports were used to perform an ELISA assay for the presence and amount of HBxAb in a variety of human sera. One hundred μl of each serum diluted 1:50 in T-wash were admixed into a polypeptide-coated well. The resulting solid-liquid phase immunoreaction admixture was maintained at 37° C. for 2 hours to permit formation of polypeptide-containing immunoreaction products. The wells were then rinsed 4 times with PBS containing 0.05% Tween-20, followed by a final rinse in deionized water (ph 6), thereby separating any polypeptide-containing (solid-phase) immunoreaction products from nonreacted human antibodies. Three hundred μl of a horseradish peroxidase-labeled goat anti-human IgG (Ortho Diagnostic Systems, Inc., Raritan, NH), diluted 1:5000 in T-wash were then admixed into each well. The resulting labeling-reaction admixtures (second solid-liquid phase admixtures) were then maintained for 1 hour at 37° C. to permit formation of polypeptide-containing (solid phase-bound) labeled immunoreaction product. The wells were then rinsed as described before to remove non-reacted labeled-antibody.

One hundred μl of o-phenylenediamine (OPD) were then admixed into each well to form a developing reaction admixture. After maintaining the developing reaction admixture for 30 minutes at about 20° C., 50 μl of 4N $H_2SO_4$ were admixed into each well to stop the developing reaction, and the resulting solutions were assayed for absorbance at 490 nanometers (nm) using a microtiter plate reader.

2. ELISA Assays to Detect the Presence of HBxAb

A total of 130 serum samples were assayed for the presence of HBxAb using the ELISA systems and methods described in Example 1. The samples were grouped according to the diagnosis of the patient at the time of collection. All serum samples from patients chronically infected with HBV (HBsAg-positive) were from Tokyo, Japan. The normal serum panel was obtained from the General Clinical Research Center (GCRC) Scripps Clinic, La Jolla, Calif. Acute phase hepatitis B serum samples were from both Tokyo and La Jolla. The serum samples were classified as acute hepatitis B (AH(B)); asymptomatic carrier (ASC); chronic hepatitis (CH); hepatocellular carcinoma (HCC) or normal. Table 1 summarizes the results obtained with serum samples assayed using each of the X polypeptides. A positive score was recorded if the sample was reactive with either one or more of the polypeptides.

TABLE 1

| Diagnosis[1] | # Samples Assayed | # Reactive With One or More Peptides | % of Total[2] |
|---|---|---|---|
| AH(B) | 21 | 0 | 0 |
| ASC | 26 | 7 | 26.9 |
| CH | 26 | 8 | 30.7 |
| HCC | 21 | 18 | 85.7 |
| Normal | 36 | 0 | 0 |
|  | 130 | 33 | 25.3 |

[1]Diagnosis of patient at the time of screen sample collection: AH(B) = acute hepatitis B; ASC = asymptomatic carrier; CH = chronic hepatitis; HCC = hepatocellular carcinoma; Normal = no detectable previous exposure to HBV (HBsAb negative).
[2]Percentage of each category of sera that tested positive against at least one polypeptide.

As can be seen from Table 1, no HBxAb was detected in the twenty-one acute phase serum samples assayed. Samples from the asymptomatic and chronic carrier groups contained approximately the same percentage of positive samples (26.9% and 30.7%, respectively). A significant number of samples 85.7%) from the hepatocellular carcinoma group (HCC) were found to contain HBxAb. The high number of positive samples within the HCC group was consistent with previous studies in which eight of eleven serum samples from patients with HCC were reactive with peptides 100–115 and 144–154 (Moriarty et al., *Science*, 227: 429–433 (1985)). All samples positive for HBxAb were HBsAg-positive as well. The HBeAg/HBeAb status had no influence on the predictability of HBxAb detection; approximately two-thirds of the positive samples were HBeAb-positive.

The absorbance values ($A_{490}$) of the positive samples are shown in Table 2 to illustrate the polypeptides to which the antibody response of each serum sample were directed.

TABLE 2

DETECTION OF HBx ANTIBODY IN HUMAN SERA

| Dx[1] | No.[2] | P8[3] | P42 | P79 | P99 | P100 | P142 |
|---|---|---|---|---|---|---|---|
| ASC | 210 | | | 0.478 | | | |
| ASC | 216 | | | 0.258 | 0.306 | 0.327 | |
| ASC | 220 | | | 0.567 | | | |
| ASC | 230 | | | 1.167 | 0.484 | 0.843 | |
| ASC | 231 | | | 0.490 | | | |
| ASC | 239 | | | 0.303 | | | |
| ASC | 245 | | | 0.627 | | | |
| CH | 204 | | | 0.478 | | | |
| CH | 212 | 0.203[4] | 0.402 | 0.356 | 0.507 | 0.333 | 0.424 |
| CH | 213 | | 0.294 | 0.269 | | | |
| CH | 219 | 0.348 | 0.549 | 0.483 | 0.235 | 0.206 | 0.325 |
| CH | 223 | | | 0.277 | | 0.349 | |
| CH | 234 | | | | 0.300 | | |
| CH | 253 | | 0.521 | | 0.328 | | |
| CH | 250B | 0.393 | 0.964 | 1.006 | 0.457 | 0.614 | 0.311 |
| HCC | 257B | 0.286 | 0.402 | 0.445 | 0.476 | 0.650 | |
| HCC | 258B | 0.369 | 0.517 | 0.304 | 0.318 | 0.407 | |
| HCC | 259B | 0.312 | | 0.528 | | 0.628 | |
| HCC | 260B | 0.292 | | 0.477 | | 0.290 | |
| HCC | 261B | 0.365 | 0.344 | 0.465 | 0.347 | 0.325 | |
| HCC | 263B | | | 1.178 | 0.309 | 0.494 | |
| HCC | 265B | 0.314 | 0.278 | 0.357 | | 0.271 | |
| HCC | 266B | 0.355 | 0.400 | 0.610 | 0.520 | 0.749 | |
| HCC | 267B | 0.586 | 0.607 | 0.749 | 0.516 | 0.643 | 0.348 |
| HCC | 268B | 0.472 | 0.255 | 0.512 | | 0.883 | 0.248 |
| HCC | 269B | 1.126 | 0.346 | 0.600 | 0.411 | 0.845 | 0.247 |
| HCC | 270B | | | 2.047 | 0.324 | 0.292 | |
| HCC | 271B | | | | 0.363 | 0.409 | |

[1] Diagnosis of patient at time of sample collection: ASC = asymptomatic carrier; CH = chronic hepatitis B; HCC = hepatocellular carcinoma.
[2] Serum accession number.
[3] Polypeptide used as solid-phase antigen in the ELISA.
[4] Absorbance value obtained in the ELISA as measured at 490 nm.

Table 2 illustrates that the specificity of the HBxAb in the ASC group was between amino acid residues 79–131 of the HBx protein, with a "hot spot" around the 79–99 region, i.e. polypeptide 79. Interestingly, serum samples from individuals who had evidence of liver damage (CH and HCC groups), contained HBxAb with a specificity covering the entire protein; i.e., most of these samples were reactive with all six peptides. The significance of this finding is unclear but suggests that perhaps HBxAg exists in more than one conformation in the different disease states.

3. Assaying Serial Samples of Acute Hepatitis B Sera for HBxAb

The lack of detectable HBxAb in one particular group of serum samples from patients with acute HBV infections (AH(B) in Table 1) suggested a study to determine whether the twenty-six samples analyzed from this group were collected at a time point too early in the infection to detect HBxAb, or indeed the appearance of antibody reflects a chronic infection with HBV. Serial serum samples were obtained from four individuals acutely infected with HBV. The time points of the samples begin at the onset of symptoms and continue up to the appearance of HBsAb. The serial samples were examined for the presence of HBxAb by ELISA assays using polypeptides 79, 99 and 100 as described in Example 1.

All four panels were negative for HBxAb at all stages of the acute infection. However, while no substantial HBxAb levels were detected, the classical markers of an acute HBV infection were observed; i.e., early detection of HBsAg, seroconversion to HBsAb by six months, with eventual viral clearance as evidenced by the detection of HBeAb. Thus, while it is not known at this time if the X protein is expressed during the replication stage of the virus, the above data suggest that the appearance of HBxAb is more closely associated with chronic HBV infection.

In these studies, the HBsAg and HBsAb levels were determined by passive hemagglutination assays according to the method of Vyas et al., Science, 170: 332–333 (1970). HBeAg and HBeAb levels were determined using a commercially available kit from Abbott Laboratories, Inc., Chicago, Ill. PreSAg levels were determined by an ELISA assay in which a PreS2- specific monoclonal antibody was affixed to microtiter plate wells (100 nanograms per well). The solid phase-bound monoclonal antibody was admixed and reacted with the serum samples to form an immunoreaction product that was detected using a horseradish peroxidase labeled anti-HBs monoclonal antibody using the conditions described in Example 1.

The foregoing is intended as illustrative of the present invention but not limiting. Numerous variations and modifications may be effected without departing from the true spirit and scope of the novel concepts of the invention.

We claim:

1. A receptor molecule that includes an antibody combining site that specifically binds both with HBxAg and with an antigenic synthetic polypeptide selected from the group consisting of polypeptides represented by the formulae:

(a) Leu-Ser-Ala-Met-Ser-Thr-Thr-Asp-Leu-Glu-Ala-Tyr-Phe-Lys-Asp-Cys;

(b) Cys-Leu-Phe-Lys-Asp-Trp-Glu-Glu-Leu-Gly-Glu-Glu-Ile-Arg-Leu-Lys-Val; and (c) Ala-Pro-Ala-Pro-Cys-Asn-Phe-Phe-Thr-Ser-Ala, wherein said receptor molecule is an antibody, a substantially whole antibody, a Fab fragment, or a (Fab')$_2$ fragment.

2. A diagnostic assay system for determining the presence of HBxAg in a body sample, said system having at least one container of a first reagent, said first reagent comprising receptor molecules that include an antibody combining site that specifically binds both with HBxAg and with an antigenic synthetic polypeptide selected from the group consisting of polypeptides represented by the formulae:

(a) Leu-Ser-Ala-Met-Ser-Thr-Thr-Asp-Leu-Glu-Ala-Tyr-Phe-Lys-Asp-Cys;

(b) Cys-Leu-Phe-Lys-Asp-Trp-Glu-Glu-Leu-Gly-Glu-Glu-Ile-Arg-Leu-Lys-Val; and (c) Ala-Pro-Ala-Pro-Cys-Asn-Phe-Phe-Thr-Ser-Ala, wherein said receptor molecule is an antibody, a substantially whole antibody, a Fab fragment, or a (Fab')$_2$ fragment.

3. The diagnostic assay system of claim 2, further comprising a second reagent in a second container, said second reagent comprising said antigenic synthetic polypeptide with which said receptor specifically binds.

4. The diagnostic assay system of claim 2, further comprising an indicating means for signalling the specific binding between said receptors and HBxAg.

5. A method of assaying for the presence of HBxAg or a polypeptide portion thereof in a body sample, comprising the steps of:

(a) admixing said body sample with receptor molecules to form an immunoreaction admixture, wherein said receptor molecules are antibodies, substantially whole antibodies, Fab fragments, (Fab')$_2$ fragments, or a combination thereof, and include an antibody combining site that specifically binds both with HBxAg and with an antigenic synthetic polypeptide selected from the group consisting of polypeptides represented by the formulae:
  (i) Leu-Ser-Ala-Met-Ser-Thr-Thr-Asp-Leu-Glu-Ala-Tyr-Phe-Lys-Asp-Cys;
  (ii) Cys-Leu-Phe-Lys-Asp-Trp-Glu-Glu-Leu-Gly-Glu-Glu-Ile-Arg-Leu-Lys-Val; and
  (iii) Ala-Pro-Ala-Pro-Cys-Asn-Phe-Phe-Thr-Ser-Ala;
(b) maintaining said admixture for a time period sufficient to form an immunoreaction product; and
(c) determining the presence of immunoreaction product formed in step (b), and thereby determining the presence of HBxAg or a polypeptide portion thereof in the body sample, wherein said polypeptide portion has an amino acid sequence corresponding to one or more antigenic determinants of HBxAg.

6. The method of claim 5, wherein said HBxAg or said polypeptide portion of HBxAg in said body sample is affixed to a solid support, said immunoreaction admixture comprises a liquid phase and a solid phase, and said immunoreaction product is formed in the solid phase.

7. The method of claim 6, wherein said solid support is comprised of nitrocellulose.

8. The method of claim 6, wherein said solid support is a microtiter plate.

9. The method of claim 5, wherein said step (c) is performed by the steps of:
  (i) admixing said immunoreaction product with an indicating means to form a second reaction admixture;
  (ii) maintaining said second admixture for a time period sufficient for said indicating means to bind to said immunoreaction product to form a second reaction product; and
  (iii) determining the presence of said indicating means in said second reaction product, thereby determining the presence of said immunoreaction product formed in step (b).

10. The method of claim 9, wherein said indicating means is a labelled antibody.

11. The method of claim 5, wherein said body sample is serum.

12. A method of assaying for the presence of anti-HBxAg antibodies present in a body sample, comprising the steps of:
  (a) providing an antigen affixed to a solid matrix to form a solid support, said antigen being selected from the group consisting of:
    (i) HBxAg in substantially purified form;
    (ii) a substantial polypeptide portion of HbxAg, wherein said portion is a polypeptide having a molecular weight of approximately 24,000 daltons that is expressed by cells transfected with a vector having ATCC accession number 40102;
    (iii) a polypeptide comprising up to about 40 amino acid residues and including the sequence Leu-Ser-Ala-Met-Ser-Thr-Thr-Asp-Leu-Glu-Ala-Tyr-Phe-Lys-Asp-Cys;
    (iv) a polypeptide comprising up to about 40 amino acid residues and including the sequence Cys-Leu-Phe-Lys-Asp-Trp-Glu-Glu-Leu-Gly-Glu-Glu-Ile-Arg-Leu-Lys-Val; and
    (v) a polypeptide comprising up to about 40 amino acid residues and including the sequence Ala-Pro-Ala-Pro-Cys-Asn-Phe-Phe-Thr-Ser-Ala;
  (b) admixing said solid support with a liquid body sample to be assayed to form solid and liquid phases;
  (c) maintaining said admixture for a time period sufficient for anti-HBxAg antibodies present in the body sample to specifically bind with the antigens of said solid support; and
  (d) determining the presence of said specific binding with an indicating means.

13. The method of claim 12, wherein said solid matrix is comprised of nitrocellulose.

14. The method of claim 12, wherein said solid matrix is a microtiter plate.

15. The method of claim 12, wherein said body sample is serum.

16. The method of claim 12, wherein said indicating means is a labeled antibody, antibody combining site or *S. aureus* protein A that reacts with said anti-HBxAg antibody.

* * * * *